United States Patent
Keitz et al.

(10) Patent No.: US 12,312,628 B2
(45) Date of Patent: May 27, 2025

(54) METABOLIC CONTROL OVER ORGANOMETALLIC CATALYSTS USING ELECTROACTIVE BACTERIA

(71) Applicant: THE BOARD OF REGENTS OF THE UNIVERSITY OF TEXAS SYSTEM, Austin, TX (US)

(72) Inventors: Benjamin Keitz, Austin, TX (US); Gang Fan, Austin, TX (US); Chris Dundas, Austin, TX (US); Austin Graham, Austin, TX (US); Nathaniel Lynd, Austin, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 525 days.

(21) Appl. No.: 15/733,681

(22) PCT Filed: Mar. 26, 2019

(86) PCT No.: PCT/US2019/024136
§ 371 (c)(1),
(2) Date: Sep. 28, 2020

(87) PCT Pub. No.: WO2019/191135
PCT Pub. Date: Oct. 3, 2019

(65) Prior Publication Data
US 2021/0017552 A1 Jan. 21, 2021

Related U.S. Application Data

(60) Provisional application No. 62/647,996, filed on Mar. 26, 2018.

(51) Int. Cl.
*C12P 7/62* (2022.01)

(52) U.S. Cl.
CPC ........................ *C12P 7/62* (2013.01)

(58) Field of Classification Search
None
See application file for complete search history.

(56) References Cited

U.S. PATENT DOCUMENTS

| 2008/0311072 A1 | 12/2008 | Karim et al. |
| 2011/0269169 A1 | 11/2011 | Li et al. |
| 2014/0004578 A1 | 1/2014 | Bond et al. |

FOREIGN PATENT DOCUMENTS

| IN | 1302/KOL/2013 A | 9/2013 |

OTHER PUBLICATIONS

Matyjaszewski et al., "Diminishing catalyst concentration in atom transferradical polymerization with reducing agents", Proc. Natl. Acad. Sci. 103:15309-15314, 2006 (Year: 2006).*
Jensen et al., ACS Synth. Biol. 5:679-688, 2016 (Year: 2016).*
Mosnáček et al., Polymers 6:2862-2874, 2014 (Year: 2014).*
Magennis et al., Nat. Mater. 13:748-755, 2014 (Year: 2014).*
West et al., "Engineering a Native Inducible Expression System in Shewanella oneidensis to Control Extracellular Electron Transfer", ACS Synth. Biol. 6:1627-1634, 2017 (Year: 2017).*
Golitsch et al., "Proof of principle for an engineered microbial biosensor based on Shewanella oneidensis outer membrane protein complexes", Biosensors and Bioelectronics 47:285-291, 2013 (Year: 2013).*
Boyer et al., "Copper-Mediated Living Radical Polymerization (Atom Transfer Radical Polymerization and Copper(0) Mediated Polymerization): From Fundamentals to Bioapplications", Chem. Rev. 116:1803-1949, 2016 (Year: 2016).*
Fan, G. "Controlled Radical Polymerization by the Electrochemically-Active Bacteria Shewanella oneidensis", Dissertation, University of Texas at Austin, 2019 (Year: 2019).*
Gorby, et al., "Electrically Conductive Bacterial Nanowires Produced by Shewanella Oneidensis Strain MR-1 and Other Microorganisms," PNAS, 103(30); 11358-11363, 2006.
International Preliminary Report on Patentability Issued in Corresponding PCT Patent Application No. PCT/US2019/024136, dated Sep. 29, 2019.
International Search Report and Written Opinion Issued in Corresponding PCT Patent Application No. PCT/US2019/024136, dated Jul. 23, 2019.
Marshall, et al., "C-Type Cytochrome-Dependent Formation of U(IV) Nanoparticles by Shewanella Oneidensis," *Plos Biol*, 4(8): e268-10, 2006.
Niu, et al., "Engineering Live Cell Surfaces with Functional Polymers Via Cytocompatible Controlled Radical Polymerization," *Nat Chem*, 9(6): 537-545, 2017.

* cited by examiner

*Primary Examiner* — David Steadman
(74) *Attorney, Agent, or Firm* — Norton Rose Fulbright US LLP

(57) ABSTRACT

Disclosed herein is a method for effecting atom or group transfer polymerization comprising polymerizing one or more radically-polymerizable monomers in the presence of a system comprising an electrically active micro-organism, a transition metal catalyst, one or more radically-polymerizable monomers, and a radical initiator. Micro-organism respiratory electron flux is harnessed to control the performance of a metal-catalyzed polymerization. The bacterial electron transport pathways of the electroactive micro-organisms can be engineered to tune and adapt various function of the electroactive micro-organism and its role in polymerization. Polymerization may be accomplished under aerobic or anaerobic conditions. Freshly cultured micro-organisms or lyophilized micro-organisms may be used to direct polymerization.

7 Claims, 15 Drawing Sheets

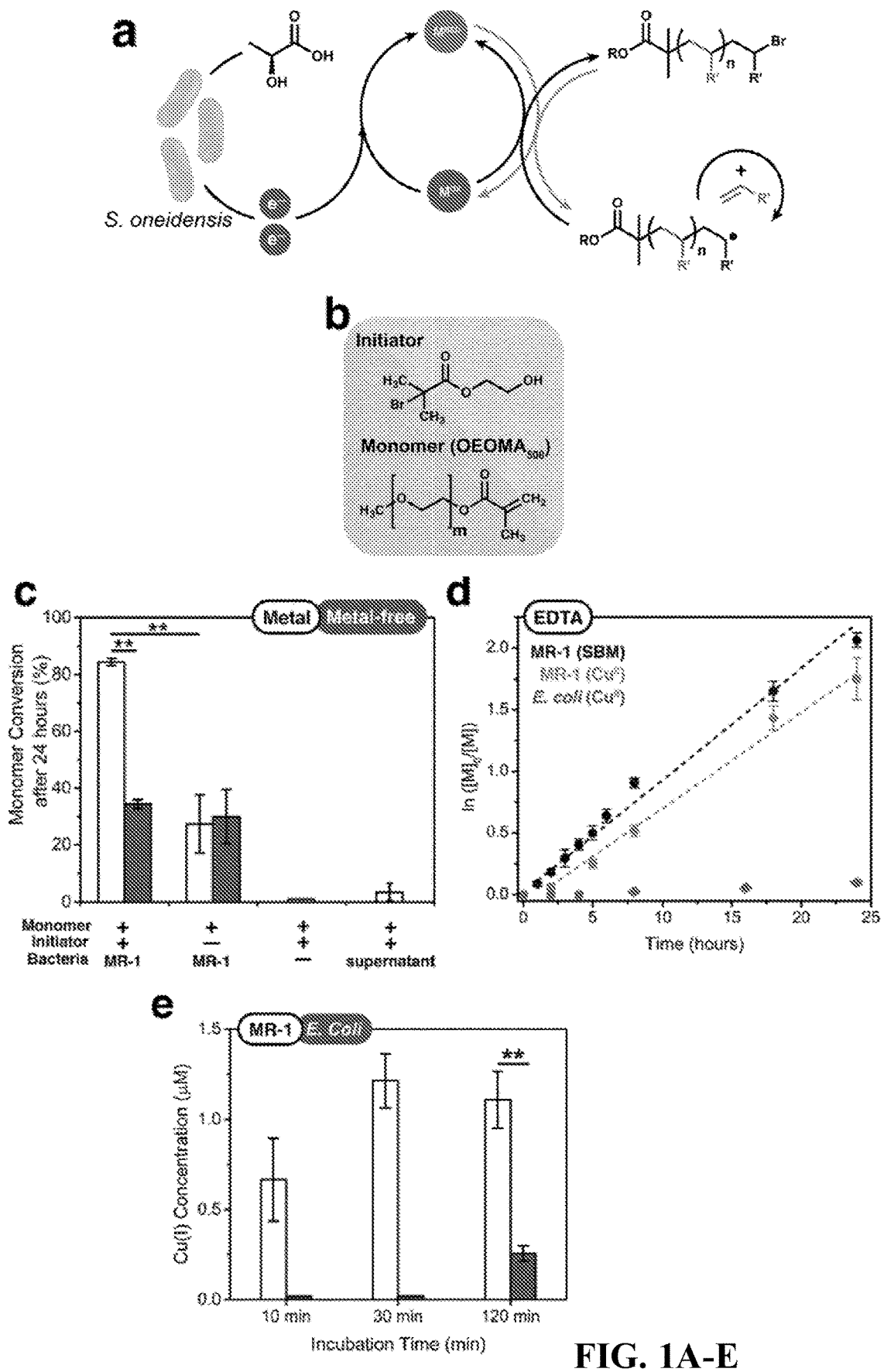
FIG. 1A-E

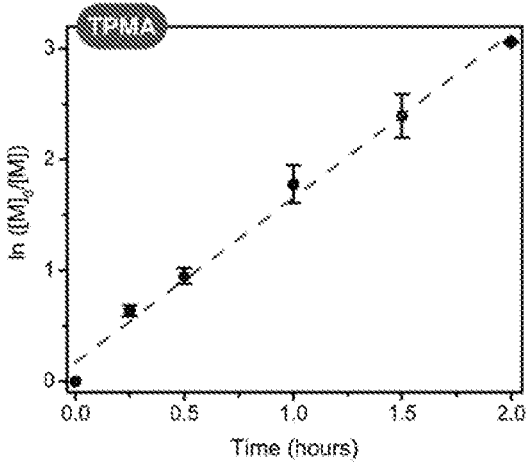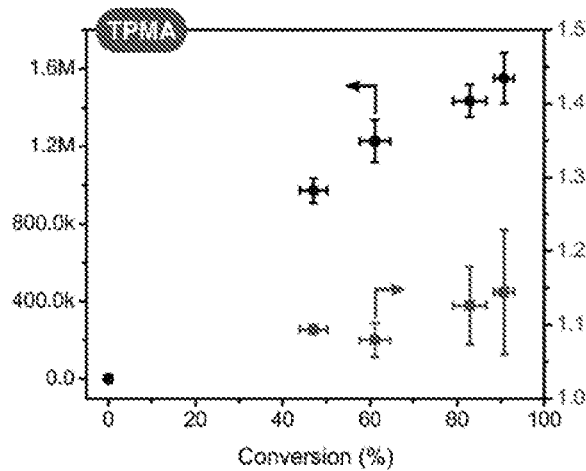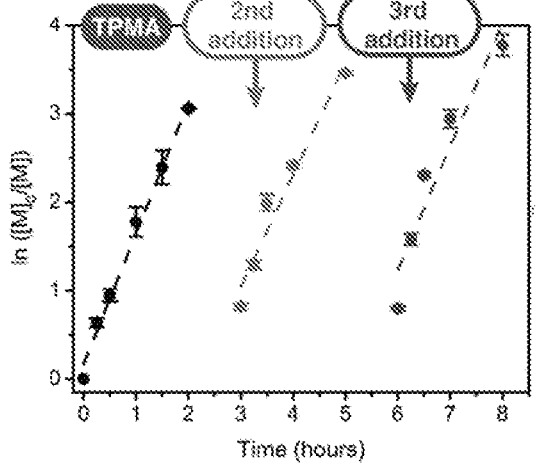
FIG. 2A-C

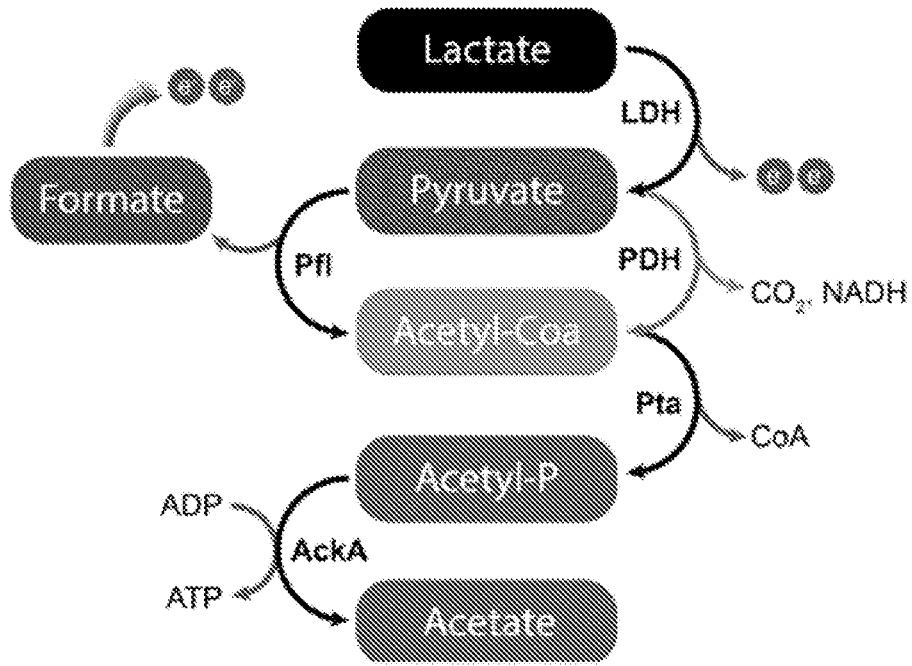
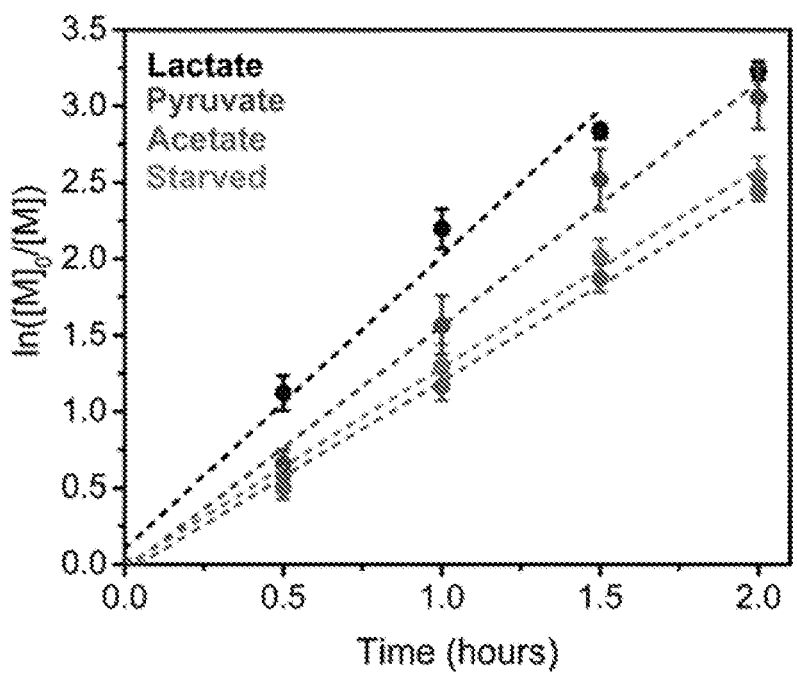
FIG. 3A-B

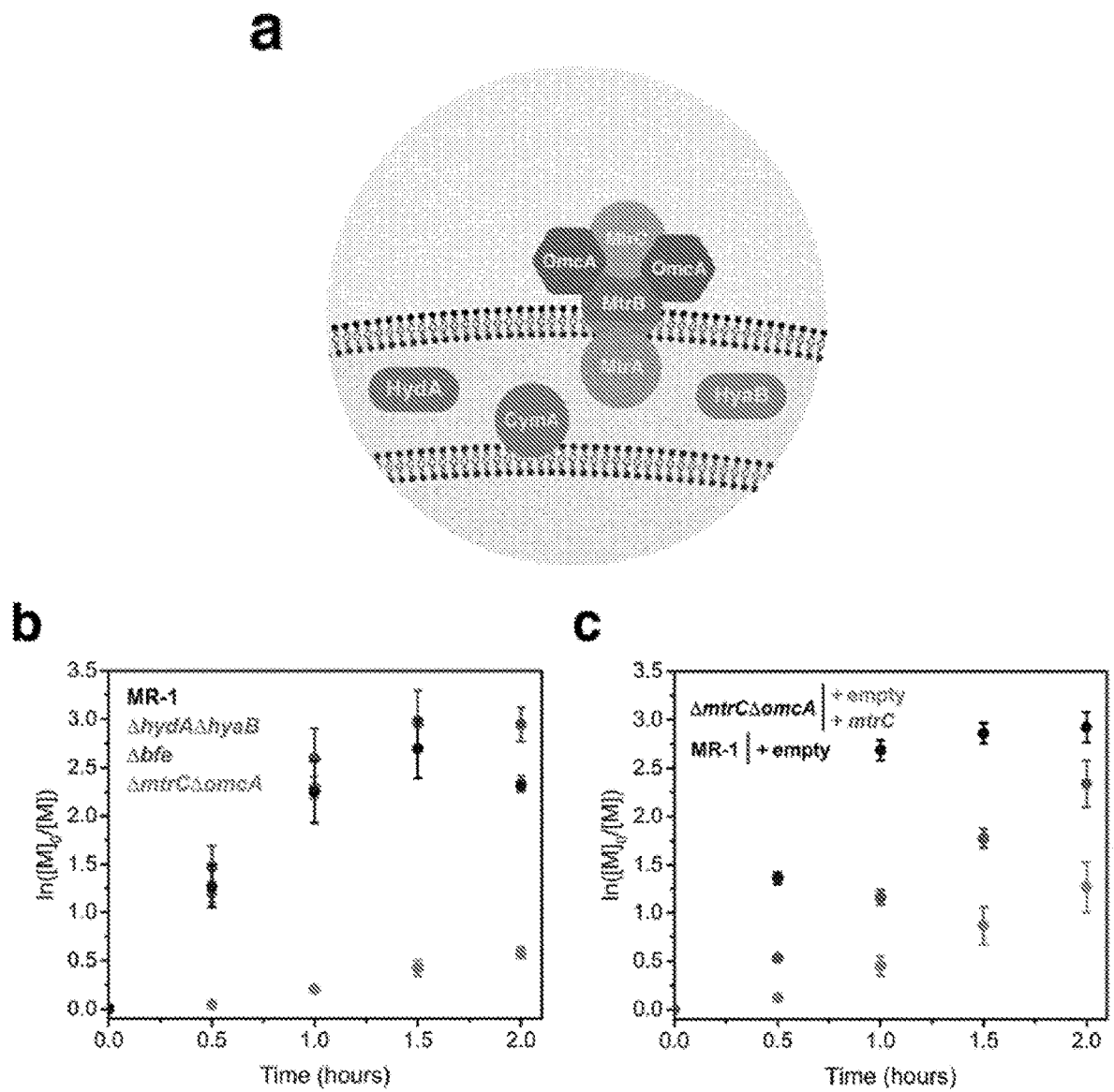
FIG. 4A-C

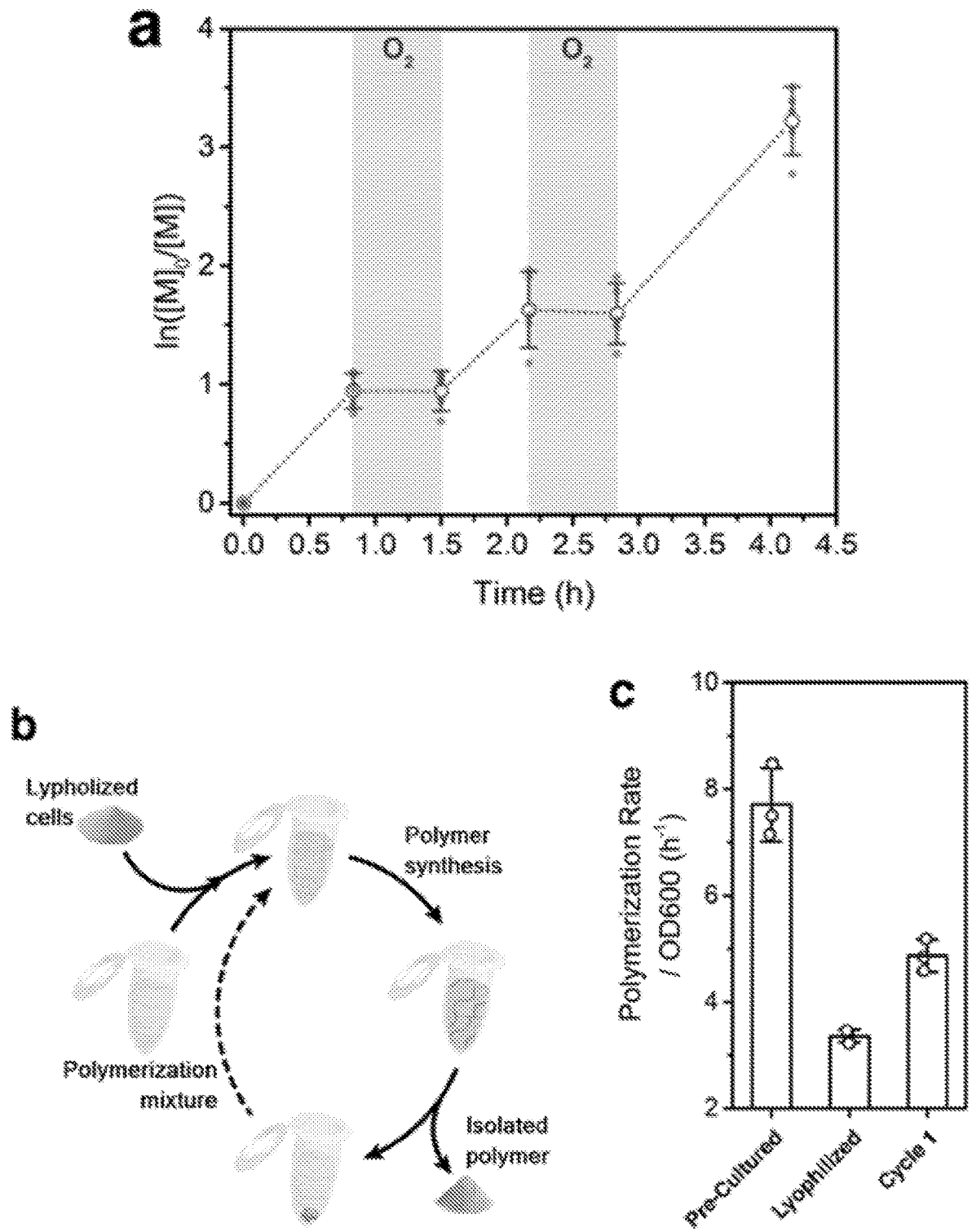
FIG. 9A-C

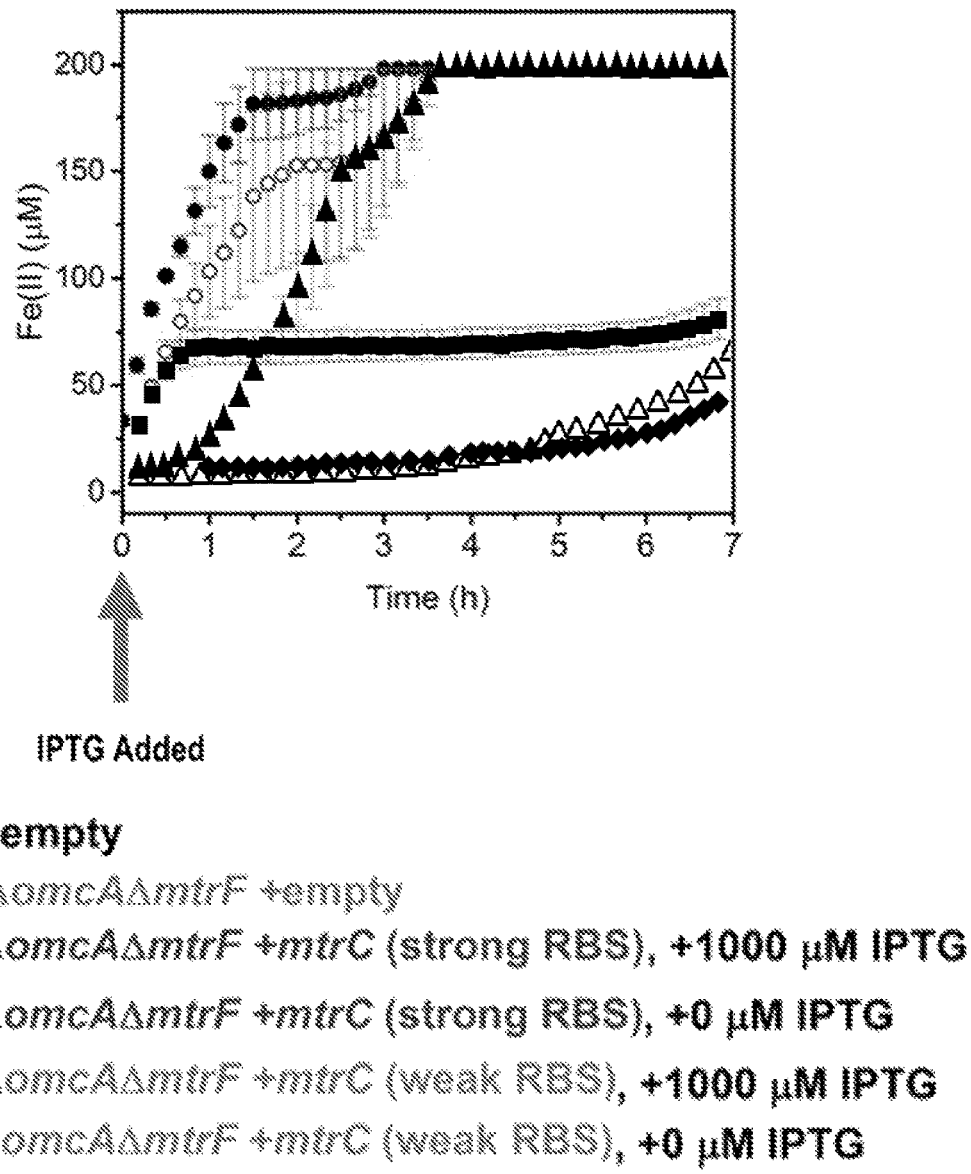
- ● MR-1 +empty
- ◆ ΔmtrCΔomcAΔmtrF +empty
- ■ ΔmtrCΔomcAΔmtrF +mtrC (strong RBS), +1000 μM IPTG
- ○ ΔmtrCΔomcAΔmtrF +mtrC (strong RBS), +0 μM IPTG
- ▲ ΔmtrCΔomcAΔmtrF +mtrC (weak RBS), +1000 μM IPTG
- △ ΔmtrCΔomcAΔmtrF +mtrC (weak RBS), +0 μM IPTG
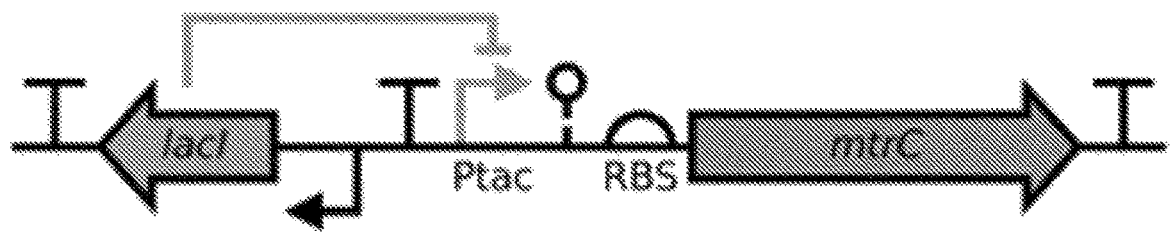
FIG. 12

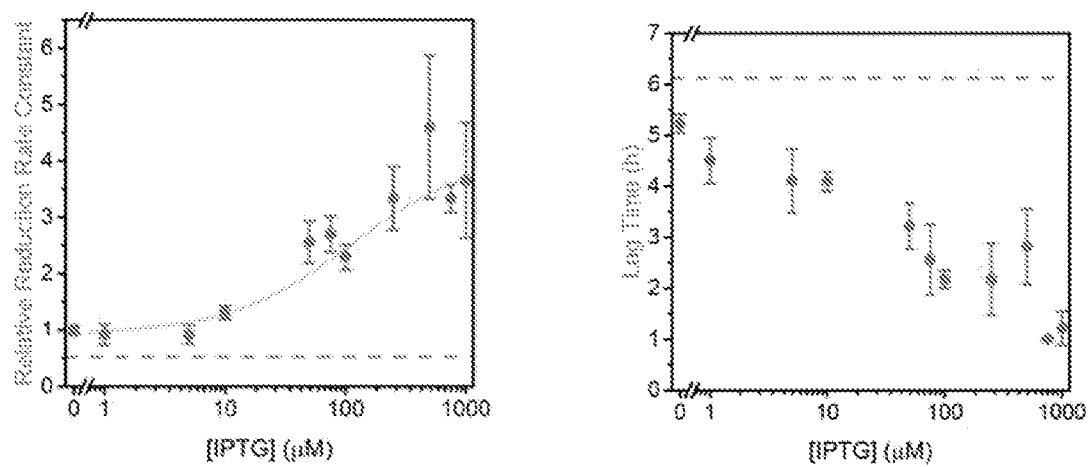
Dashed line = empty plasmid control
● ΔmtrCΔomcAΔmtrF +mtrC (weak RBS)
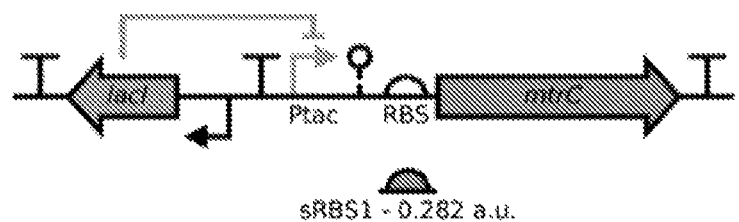
FIG. 13

METABOLIC CONTROL OVER ORGANOMETALLIC CATALYSTS USING ELECTROACTIVE BACTERIA

CROSS-REFERENCE TO RELATED APPLICATIONS

This application is a national phase application under 35 U.S.C. § 371 of International Application No. PCT/US2019/024136, filed Mar. 26, 2019, which claims benefit of priority to U.S. Provisional Patent Application No. 62/647,996 filed Mar. 26, 2018, which is incorporated herein by reference in its entirety.

FIELD OF THE INVENTION

The present disclosure relates to the fields of cell biology, organometallic catalysis, metabolic engineering, and synthetic biology.

BACKGROUND

Synthetic biology is an interdisciplinary area that involves the application of engineering principles to biology. By combining the fields of chemistry, biology, computer science, and engineering, synthetic biology can be used to modify molecular, cell, and systems biologies. This includes the design and construction of new biological parts, devices, and systems, as well as the re-design of existing, natural biological systems for useful purposes.

Metabolic engineering involves directed modulation of metabolic pathways for metabolite over-production or alteration of natural products. Metabolic pathways use a series of biochemical reactions and enzymes that allow cells to convert raw materials into molecules necessary for cell survival. Metabolic engineering employs metabolism-modulating strategies like overexpressing a gene encoding the rate-limiting enzyme of a biosynthetic pathway, blocking a competing metabolic pathway, heterologous gene expression, and enzyme engineering. By rationally tuning or modifying metabolic pathways, metabolic engineering can be used to produce valuable substances on an industrial scale in a cost-effective manner.

Metabolic engineering and synthetic biology benefit from the tunable and tightly controlled transformations afforded by biological systems. Despite significant progress, the reaction space provided by these areas is still relatively limited when compared to traditional and well-established synthetic chemical reactions. Metabolic engineering reactions have generally been limited to naturally occurring pathways and products.

Metabolic engineering and transition metal catalysis are traditionally viewed as competing industrial processes. Metal catalysis benefits from well-defined chemical mechanism but usually requires high temperatures, pressures, and organic solvents. Metabolic engineering takes advantage of the flexibility and genetic tunability of microorganisms but is limited to well-defined metabolic pathways and genetically tractable chassis organisms (e.g., E. coli).

It would be beneficial to combine biological techniques stemming from recent advances in synthetic biology and metabolic engineering with traditional metal-catalyzed processes. The conglomeration of well-known transition metal catalyzed reactions with the variability and tunability of biological organisms would afford a multitude of new approaches for the production of known products. Industrial processes that were previously not amenable to biological approaches could be realized by combining engineered organisms with traditional chemical techniques.

SUMMARY

A discovery has been made that combines certain aspects of synthetic biology, metabolic engineering, and transition-metal catalysis by taking advantage of the specialized electron transport machinery in electroactive bacteria. Electrons generated from bacterial metabolism may be used to reduce a metal catalyst and turn-over or control a catalytic cycle. Genetic factors and proteins that participate in biological electron transfer can be manipulated to influence catalysis. Similarly, the structure of the metal catalyst can be changed to enhance or deemphasize the role of the bacteria. This concept is applied herein to polymerization, and is applicable to a variety of additional reactions that involve electron transport.

In some aspects, a method for effecting atom or group transfer polymerization is provided. The method comprises polymerizing one or more radically-polymerizable monomers in the presence of a system comprising an electrically active micro-organism, a transition metal catalyst, one or more radically-polymerizable monomers, and a radical initiator. In some embodiments, the electrically active microorganism is Shewanella oneidensis. The transition catalyst may comprise a metal selected from the group consisting of copper, cobalt, iron, and manganese. Exemplary, non-limiting examples of the transition metal catalyst include $CuSO_4$, $Co(NO_3)_2$, $FeSO_4$, $MnSO_4$, or a hydrate thereof.

In some embodiments, the one or more radically-polymerizable monomers is a monomer of formula I:

(I)

wherein $R^1$ and $R^2$ are independently selected from the group consisting of H, halogen, CN, $CF_3$, straight or branched alkyl of 1 to 20 carbon atoms, aryl, $\alpha,\beta$-unsaturated straight or branched alkenyl or alkynyl of 2 to 10 carbon atoms, $\alpha,\beta$-unsaturated straight or branched alkenyl of 2 to 6 carbon atoms wherein at least one hydrogen atoms is substituted with a halogen, $C_3$-$C_8$ cycloalkyl, phenyl which may optionally have from 1-5 substituents on the phenyl ring, heterocyclyl, C(=Y)$R^5$, C(=Y)$NR^6R^7$, $YCR^6R^7R^8$ and YC(=Y)$R^8$, where Y may be $NR^8$ or O, R5 is alkyl of from 1 to 20 carbon atoms, alkoxy of from 1 to 20 carbon atoms aryloxy or heterocyclyloxy, $R^6$ and $R^7$ are independently H or alkyl of from 1 to 20 carbon atoms, or $R^6$ and $R^7$ may be joined together to form an alkylene group of from 2 to 5 carbon atoms, thus forming a 3- to 6-membered ring, and $R^8$ is H, straight or branched $C_1$-$C_{20}$ alkyl and aryl; and $R^3$ is selected from the group consisting of H, halogen, $C_1$-$C_6$ alkyl, CN, COO$R^9$; where $R^9$ is H, an alkali metal, or a $C_1$-$C_6$ alkyl group or aryl; or $R^1$ and $R^3$ may be joined to form a group of the formula $(CH_2)_{n'}$, which may be substituted with from 1 to 2n' halogen atoms or $C_1$-$C_4$ alkyl groups or C(=O)—Y—C(=O), where n' is from 2 to 6 and Y is defined as above; or $R^4$ is the same as $R^1$ or $R^2$ or optionally $R^4$ is a CN group; and at least two of $R^1$, $R^2$, and $R^3$ are H or halogen. In some embodiments, the monomer is a styrene, isobutylene, vinyl ether, acrylate, methacrylate, acrylonitrile, acrylamide, vinyl chloride, or a tetrafluoroethylene.

In some aspects, the initiator comprises one or more radically transferrable atoms or groups. A radically transferrable atom or group is an atom or chemical functional group that may separate or be separated from the molecule to which it is bound having a single, unpaired electron (radical). The initiator may be represented by formula II:

$$R^{11}R^{12}R^{13}C-Z' \quad (II)$$

where Z' is selected from the group consisting of Cl, Br, I, $OR^{10}$ (where $R^{10}$ is alkyl of from 1 to 20 carbon atoms, in which each of the hydrogen atoms may be independently replaced by halide, preferably fluoride or chloride), $SR^{14}$, $SeR^{14}$, —SCN (thiocyanate), $OC(=O)R^{14}$, $OP(=O)R^{14}$, $OP(=O)(OR^{14})_2$, $OP(=O)OR^{14}$, $O-N(R^{14})_2$ and $S-(=S)N(R^{14})_2$, where $R^{14}$ is aryl or a straight or branched C1-C20 alkyl group, or when an $N(R^{14})_2$ group is present, the two $R^{14}$ groups may be joined to form a 5-, 6-, or 7-member heterocyclic ring; and $R^{11}$, $R^{12}$, and $R^{13}$ are each independently selected from the group consisting of H, halogen, $C_1$-$C_{20}$ alkyl, $C_3$-$C_8$ cycloalkyl, $C(=Y)R^5$, $C(=Y)NR^6R^7$ (where $R^5$-$R^7$ are as defined above), COCl, OH, CN, $C_2$-$C_{20}$ alkenyl or alkynyl, oxiranyl, glycidyl, aryl, heterocyclyl, aralkyl, aralkenyl (aryl-substituted alkenyl, where alkenyl is vinyl which may be substituted with one or two $C_1$-$C_6$ alkyl groups and/or halogen atoms), $C_1$-$C_6$ alkyl in which from one to all of the hydrogen atoms are replaced with a halogen) and $C_1$-$C_6$ alkyl substituted with from one to three substituents selected from the group consisting of $C_1$-$C_4$ alkoxy, aryl, heterocyclyl, $C(=Y)R^5$, $C(=Y)NR^6R^7$, oxiranyl and glycidyl; such that no more than two of $R^{11}$, $R^{12}$, and $R^{13}$ are H. Preferred initiators include alkyl halides, aralkyl halides, and haloalkyl esters. Exemplay initiators include but are not limited to 1-phenylethyl chloride, 1-phenylethyl bromide, methyl 2-chloropropionate, ethyl 2-chloropropionate, methyl 2-bromopropionate, ethyl 2-bromoisobutyrate 1-phenylethyl chloride and 1-phenylethyl bromide (e.g., where $R^{11}$=Ph $R^{12}$=CH$_3$, $R^{13}$=H and X=Cl or Br), chloroform, carbon tetrachloride, 2-bromopropionitrile, $C_1$-$C_6$ alkyl esters of a 2-halo-$C_1$-$C_6$-carboxylic acid (such as 2-chloropropionic acid, 2-bromopropionic acid, 2-chloroisobutyric acid, 2-bromoisobutyric acid, etc.) and compounds of the formula $C_6H_x(CH_2Y')_y$, where Y' is Cl or Br, x+y=6, and Y≥1.

In some embodiments, the transition metal catalyst comprises a metal selected from the group consisting of copper, cobalt, iron, and manganese. In some embodiments, the transition metal catalyst is one of $CuSO_4$, $Co(NO_3)_2$, $FeSO_4$, $MnSO_4$, or a hydrate thereof. The transition metal catalyst may further comprise at least one coordinating ligand. In a particular embodiment, the at least one coordinating ligand is tris(2-pridylmethyl)amine.

Either or both of the electrically active micro-organism and metal catalyst can be optimized. In some embodiments, the method of polymerizing one or more radically-polymerizable monomers includes reaction conditions that may be modified or adjusted to control a reaction parameter or product property. Reaction conditions that may be modified or adjusted include initial cell density, temperature, secondary electron acceptor, monomer-to-initiator ratio, carbon source, oxygen concentration, metal identity, metal concentration, metal ligan, initial total monomer concentration, and reaction medium (buffer). Reaction conditions can be modified to adjust or control reaction parameters, such as reaction kinetics. One or more reaction conditions can be modified to adjust or control a product property selected from the group consisting of polymer length, polydispersity, and polymer microstructure, e.g., block copolymers, random copolymers, etc.

In some embodiments, a method for cross linking polymers is provided. The method comprises cross-linking a polymeric starting material or producing a cross-linked polymer from one or more radically-polymerizable monomers in the presence of a system comprising an electrically active micro-organism, a transition metal catalyst, one or more radically-polymerizable monomers, and a radical initiator.

In some aspects, a method for reducing a transition metal catalyst is provided. The method comprises the step of providing an electrically active micro-organism disposed in proximity to a transition metal catalyst. The electrically active micro-organism may transfer electrons to the transition metal catalyst, thereby reducing the transition metal catalyst.

In some aspects, the electrically active micro-organism is *S. oneidensis*. In further aspects, the electrically active micro-organism is *Vibrio natriegens, Aeromonas hydrophila, Pseudomonas aeruginosa*, or Mtr-transformed *E. coli*. The electrically active micro-organism's respiratory electron flux is harnessed to provide electrons. The electrons are taken up by the transition metal catalyst transition metal, thereby reducing transition metal catalyst. The micro-organism's respiratory electron reduces the transition metal catalyst metal from an oxidized state to a reduced state. In embodiments, the transition metal catalyst reduction is a single-electron reduction that reduces a transition metal oxidation state by −1. For example, a transition metal catalyst having a copper transition metal in the +2 oxidation state may be reduced by the micro-organism's electrons such that the copper is reduced to the +1 oxidation state. This is an example of a single-electron reduction, however, multiple-electron reductions are contemplated. In some embodiments, the transition metal catalyst reduction is a single-electron reduction that reduces a transition metal oxidation state by −2.

Because *S. oneidensis* can rapidly transition from aerobic to anaerobic respiration, this organism can metabolically control living radical polymerizations under aerobic conditions by first consuming dissolved oxygen, then directing extracellular electron transfer flux to a metal catalyst. In some embodiments *S. oneidensis* directs living radical polymerizations under anaerobic conditions. In other embodiments *S. oneidensis* directs living radical polymerizations under aerobic conditions.

In some embodiments, freshly cultured organisms are used to direct polymerization. In other embodiments, lyophilized organisms are used to direct polymerization.

In some embodiments, the electrically active micro-organism is provided with a carbon source. The carbon source may be lactate, N-acetylglucosamine, or other carbon sources employed in or produced by metabolic processes.

The transition metal catalyst may comprise a metal selected from the group consisting of copper, cobalt, iron, and manganese. In further embodiments, the transition metal catalyst is one of $CuSO_4$, $Co(NO_3)_2$, $FeSO_4$, $MnSO_4$, or a hydrate thereof. The transition metal catalyst may further comprise at least one coordinating ligand. In a particular embodiment, the at least one coordinating ligand is tris(2-pridylmethyl)amine.

In some embodiments, the electrically active micro-organism can be modified in order to adjust or modify its effect on polymerization. The electrically active micro-organism may be employed in polymer cross-linking. The organism's role in polymerization and/or cross-linking may be modified or "tuned" in order to favor or dis-favor certain polymer characteristics. Modification of the electrically active microorganism may be performed using synthetic biology or metabolic engineering techniques known to those of skill in the art. For example, the electrically active micro-organism may be genetically engineered to increase translation of proteins involved in electron transport. The electrically active micro-organism culture conditions may be modulated to favor a desired activity, or disfavor a non-desired activity. One non-limiting example of a favored activity is the organism's ability to cross-link a polymer. The organism may be engineered or may be provided in a culture that favors an activity or behavior.

MtrC serves as a regulator of polymerization activity in S. oneidensis. In some aspects of the disclosure, transcription of the operon containing the MtrC gene may be regulated in order to alter MtrC expression. In some aspects, the gene encoding MtrC may be engineered to confer a desired effect on the MtrC protein. For example, MtrC may be engineered to increase electron flux or perturb interaction with an organometallic catalyst. The mtr pathway includes a number of proteins and corresponding genes, including OmcA, MtrC, MtrA, MtrB, and CymA. One or more genes in the mtr pathway may be engineererd to effect bacterial growth, electron flux, catalysis, polymerization, cross-linking, etc. In some embodiments, regulation of mtr pathway operons may be adjusted in order to affect mtr gene transcription.

In some embodiments, a micro-organism includes a knocked out extracellular electron transfer gene. The knocked out gene may be at least one of OmcA, MtrC, MtrA, MtrB, MtrF, and CymA. In some embodiments a micro-organism may be transformed with a plasmid DNA construct. The plasmid DNA construct may include one or more of one of OmcA, MtrC, MtrA, MtrB, MtrF, and CymA genes. The plasmid DNA construct may be under the control of variable strength gene expression elements, including inducible promoters, repressors, and ribosome binding sites known to those of skill in the art. Exemplary, non-limiting examples include the LacI repressor and the Ptac promoter. Therefore, transcription, and downstream translation, of a plasmid DNA construct encoding one or more electron transfer genes may be controlled. In some aspects, controlling transcription of one or more electron transfer genes within a plasmid DNA construct allows a user to control polymerization and/or reduction of a transition of a transition metal catalyst. In some aspects, a small molecule may be used to induce plasmid DNA transcription. The small molecule's concentration may be varied in order to induce gene expression in a dose-dependent manner. In some aspects, the small molecule is Isopropyl β-D-1-thiogalactopyranoside (IPTG).

Any embodiment of any of the disclosed compositions and/or methods can consist of or consist essentially of— rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims and/or the specification may mean"one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the methods disclosed in this specification includes the organism's abilities initialize a polymerization reaction.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

The claims are not to be interpreted as including means-plus- or step-plus-function limitations, unless such a limitation is explicitly recited in a given claim using the phrase (s) "means for" or "step for," respectively.

BRIEF DESCRIPTION OF THE FIGURES

FIG. 1A-E. S. oneidensis enabled atom-transfer radical polymerization (ATRP) and initial polymerization kinetics: (A) Electron equivalents generated from S. oneidensis (wild type, MR-1) reduce a metal catalyst from an inactive state ($M^{OX}$) to an active state ($M^{RED}$). The active catalyst reacts with a halogenated initiator or polymer chain to produce a radical that can polymerize olefins. The radical can also react with the now-deactivated catalyst ($M^{OX}$) to form a dormant chain; (B) ATRP initiator (2-hydroxyethyl 2-bromoisobutyrate, HEBiB) and macromonomer ($OEOMA_{500}$) used in this study; (C) Monomer conversion after 24 hours under various conditions with (left bar) and without (right bar) trace metal mix added to bacterial media; (D) Kinetics of monomer conversion in MR-1 or E. coli culture using Cu(II)-EDTA as catalyst; (E) Extracellular Cu(II) reduction monitored with the Cu(I) specific fluorescent dye CF4. Data show mean±S.D. of three independent experiments. **, $P<0.01$.

FIG. 2A-C. Kinetics and properties of polymers formed with MR-1: (A) First-order kinetics for conversion of monomer over time using Cu(II)-TPMA with MR-1; (B) Molecular weight and polydispersity of poly($OEOMA_{500}$) as a function of monomer conversion; (C) Repeated addition of OEOMA$_{500}$ to the microbial culture yielded first order kinetics with rate constants consistent with the initial addition.

FIG. 3A-B. Polymerization activity is controlled by electroactive metabolism: (A) Simplified carbon metabolism of *S. oneidensis*; (B) Polymerization kinetics for MR-1 supplied with different carbon sources using Cu(II)-TPMA as catalyst. Data show mean±S.D. of three independent experiments.

FIG. 4A-C. Electron transfer proteins impact polymerization kinetics: (A) Key proteins involved in extracellular electron transport in MR-1; (B) Effect of gene knockouts on polymerization activity using Cu(II)-TPMA; (C) Rescue of normal polymerization activity via complementation with a plasmid encoding MtrC, using Cu(II)-TPMA as a catalyst. Data show mean±S.D. of three independent experiments.

FIG. 9A-C. Aerobic polymerization and lyophilized cells. (A) Polymerization stopping during oxygen bubbling followed by automatically restarting with the same rate. Individual data points are shown as semi-transparent dots, n=5. (B) Reaction scheme for polymerization using lyophilized cells and recycling. (C) Polymerization rates starting from pre-cultured, lyophilized, and cycled MR-1 cells. Data show mean±SD.

FIG. 12 The effect of IPTG and RBS sequence on inducibility of MtrC expression and Fe(III)-citrate reduction. Error bars indicate standard error of the mean for three biological replicates.

FIG. 13 Fe(III) reduction rate and lag time response functions for BUFFER GATE/'weak' RBS mtrC plasmid. Error bars indicate standard error of the mean for three biological replicates

DETAILED DESCRIPTION

Figure 5:
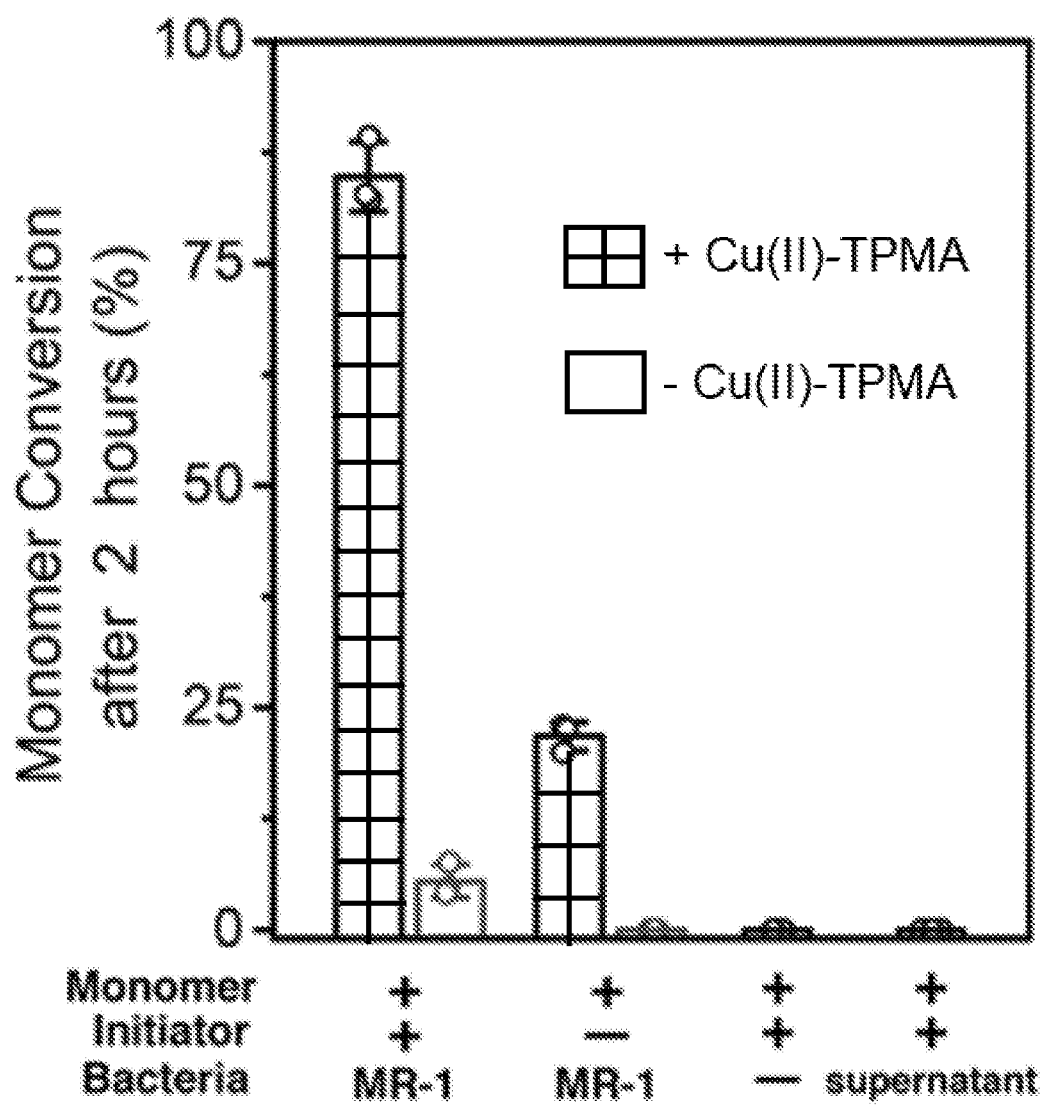
FIG. 5. Effect of different polymerization components on monomer (OEOMA$_{500}$) conversion under aerobic conditions.

Various features and advantageous details are explained more fully with reference to the non-limiting embodiments that are illustrated in the accompanying drawings and detailed in the following description. It should be understood, however, that the detailed description and the specific examples, while indicating embodiments, are given by way of illustration only, and not by way of limitation. Various substitutions, modifications, additions, and/or rearrangements will be apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O) CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "aryl" or "aromatic" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl) phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

One way to expand the scope of metabolic transformations is to leverage respiratory electron flux, which can be used for power generation, as in microbial fuel cells, or inverted to produce metabolites from exogenously-supplied electrons, as in bioelectrosynthesis. The flexibility of these applications can be extended further by coupling metabolic transformations to processes that occur independently of the cell, such as nanoparticle photoexcitation or electrocatalytic hydrogen generation. However, these advances are still limited to native metabolic intermediates and products.

In an effort to expand the power of microbial catalysis, the effect of electron flux from metabolic activity on controlling exogenous, bioorthogonal reactions via extracellular electron transfer to a redox-active metal catalyst was examined. The electroactive bacterium Shewanella oneidensis (wild-type, MR-1) was selected for its ability to transport electron equivalents over micron distances and its specialized machinery for moving electrons in and out of the cell. Under anaerobic conditions, MR-1 consumes lactate, or other small carbon sources, and deposits electrons into redox-active organics, metals, and materials. Given the relatively negative potential of its terminal outer membrane cytochromes (ca. −350 to +50 mV vs. SHE), MR-1 is able to reduce a variety of soluble metals including U(VI), Cr(VI), Fe(III), V(III), and Mn (IV), as well as oxides such as hematite, ferrihydrite, and graphene oxide. MR-1 can also respire onto electrodes poised at an appropriate potential.

Given the electroactive properties of S. oneidensis discussed above, coupling between cellular metabolism and an exogenous metal catalyzed reaction was examined. These bacteria apply an effective potential in solution that controls the oxidation state of a metal catalyst and its subsequent activity. The experimental results provided herein establish a nexus between metabolic engineering and organometallic catalysts by leveraging biological, metabolic electron transport for a non-biological, olefin polymerization process. Furthermore, the polymerization process can be tuned according to the changes of bacterial genetics, the inorganic catalyst, and metabolic inputs such as lactate and oxygen.

The novel polymerization methodology disclosed herein relies on the electroactive bacterium Shewanella oneidensis acting in concert with an inorganic catalyst. The system comprises four components, S. oneidensis, a metal catalyst, a monomer, and an initiator. The metabolic activity of S. oneidensis reduces the metal catalyst, which then activates the initiator. Once activated, the initiator adds monomer units to form a polymer chain. The rate of reaction is controlled by S. oneidensis and the structure of the metal catalyst. Neglecting any of the above components significantly reduces polymerization activity. Additionally, other common bacteria, such as E. coli, show no appreciable polymerization activity. This demonstrates that electronic communication between S. oneidensis and the metal catalyst is required to control the polymerization. The methods disclosed herein can be used for the sustainable synthesis of well-defined polymers, or for the preparation of responsive materials that change properties in response to specific biological and chemical inputs. The methods disclosed herein demonstrate a general means to control exogenous transition-metal catalyzed reactions through the metabolic engineering of electron transport chains in bacteria.

EXAMPLES

Chemicals and Reagents

Tetrakis(acetonitrile)copper(I) tetrafluoroborate (Cu($CH_3CN$)$_4BF_4$, Sigma-Aldrich, 97%), N-isopropylacrylamide (NIPAM, Sigma-Aldrich, 97%), L-Glutathione reduced (GSH, Sigma-Aldrich, 98%), Cupric sulfate pentahydrate ($CuSO_4 \cdot 5H_2O$, VWR, ACS grade), Tris(2-pyridylmethyl) amine (TPMA, Sigma-Aldrich, 98%), Copper(II) bromide ($CuBr_2$, Sigma-Aldrich, 99%), 2-Hydroxyethyl 2-bromoisobutyrate (HEBIB, Sigma-Aldrich, 95%), Sodium fumarate ($Na_2C_4H_2O_4$, Alfa Aesar, 98%) and Sodium DL-lactate ($NaC_3H_5O_3$, TCI, 60% in water) were used as received. Poly(ethylene glycol) methyl ether methacrylate (OEOMA$_{500}$, Sigma-Aldrich, average $M_n$ 500) was passed through a column filled with activated basic alumina ($Al_2O_3$, Sigma-Aldrich) to remove polymerization inhibitors immediately prior to use. OEOMA$_{900}$ (Sigma-Aldrich, average $M_n$ 950) was dissolved in THF and passed through basic alumina. The solution was then precipitated with cold hexanes and dried under reduced pressure overnight prior to use. Methanol (MeOH, Fisher Chemical, HPLC grade), N,N-Dimethylformamide (HCON($CH_3$)$_2$, Alfa Aesar, 99.7%, HPLC grade) and sodium azide ($NaN_3$, Sigma-Aldrich, 99%) were used as received for GPC characterization. Deuterium oxide ($D_2O$, Sigma-Aldrich, 99.9%) was used as received for NMR characterization. CF4 and CF4-CTRL imaging probes (1 mM) were dissolved in DMSO and stored at −20° C. Ultrapure Water was generated from a Milli-Q Integral Water Purification System.

Analysis and Measurement

Polymer samples were analyzed by gel permeation chromatography (GPC) with a Superdex 200 Increase 10/300 GL (GE Healthcare Bio-Sciences AB, Particle size ~8.6 μm) column using 20% (v/v) methanol aqueous solution (0.05 M NaCl) as the eluent (25° C.), and a 3-angle laser light scattering (MALLS) detector (Wyatt Technology, miniDAWN TREOSII). Molecular weights were determined using ASTRA software (Version: 6.0) from Wyatt Technology. The dn/dc value for poly(OEOMA$_{500}$) was obtained from the literature (0.115 mL/g). $^1$H NMR spectra of monomer/polymer solutions were collected on an Agilent 400 MHz NMR spectrometer or a Bruker Avance III 500 spectrometer using $D_2O$ as solvent.

Bacterial Strains and Culture

Anaerobic culture was performed with an incubator located inside a Coy Anaerobic Glovebox containing a humidified atmosphere of 3% hydrogen and balance nitrogen. The *Escherichia coli* strains used for cloning and conjugal transfer were maintained on lysogeny broth (LB) that was supplemented with 25 µg/mL kanamycin and 250 µM 2,6-diaminopimelic acid as necessary. During routine propagation, *Shewanella oneidensis* strains were maintained on LB agar plates containing 25 µg/mL kanamycin as necessary. For growth assays and polymerization reactions, *S. oneidensis* and *E. coli* strains were grown in *Shewanella* basal medium (SBM) supplemented with 0.05% casamino acids stock (10% w/v). SBM was supplemented with 5 mL/liter mineral mix when indicated. Cells were prepped for polymerization reactions as follows: strains stored in 20% glycerol at −80° C. were freshly streaked onto LB agar plates and aerobically incubated for ~16 h at 30° C. (*S. oneidensis*) or 37° C. (*E. coli*). Plates were brought into the anaerobic glovebox and single colonies were used to inoculate SBM supplemented with 20 mM sodium lactate and 40 mM sodium fumarate. Inoculated cultures were then incubated for ~16 h at 30° C. (*S. oneidensis*) or 37° C. (*E. coli*). Stationary-phase cultures were washed by transferring cells to centrifuge tubes inside the anaerobic chamber and spinning at 6000×g for 20 min. Supernatant was exchanged with fresh SBM supplemented with casamino acids and mineral mix (when indicated). Two washes were performed and on the final wash, cells were concentrated to a 200× stock (OD600 of 2.0). Cells were used to initiate polymerization immediately after concentration.

Dissolved Oxygen and Biomass Measurements

Dissolved oxygen and biomass were measured using a BioLector Pro (m2p-labs) and processed using the BioLection analysis software. Aerobically prepared *S. oneidensis* cultures were inoculated into SBM containing either growth reagents or polymerization mixture. Dissolved oxygen and biomass were measured using the PSt3 optode and light scattering at 30° C. with 200 rpm shaking at 85% humidity.

Example 1 mtrC Plasmid Construction and Confirmation of Functional Expression

DNA constructs were made via restriction cloning and Gibson assembly using enzymes from New England Biolabs. Plasmids, primers, and specific protocols are detailed below. Briefly, mtrC amplified from MR-1 genomic DNA was cloned into the pShew base plasmid, transformed into *E. coli* DH5α by electroporation, and sequence verified (DNA Sequencing Facility, University of Texas at Austin). Conjugation into *S. oneidensis* was performed according to literature procedures by utilizing an *E. coli* mating strain (WM3064) and sequence verified. Functional expression of MtrC was confirmed by assaying Fe(III) reduction in *S. oneidensis* strains carrying either an empty or mtrC vector. Complementation results were consistent with previous reports describing strains deficient in Fe(III) reduction.

Example 2

General Polymerization Conditions

All stock solutions and reaction mixtures were prepared in an anaerobic glovebox. Prior to polymerizations, stock solutions of HEBIB (100× stock, 2.9 µL in 287 µL SBM containing casamino acids) and Cu-EDTA (200× stock from 10 mg $CuSO_4.5H_2O$ in 1 L of 1.35 mM EDTA buffer) or Cu-TPMA (200× stock from 8.9 mg $CuBr_2$ and 11.6 mg TPMA in 100 mL DMF) were mixed. Afterwards, a 2 mL polymerization reaction mixture was prepared as follows. To a sterile polypropylene culture tube was added 60% w/w sodium lactate solution (5.7 µL), 1 M fumarate solution (80 µL), OEOMA$_{500}$ (92.6 µL, 200 µmol), HEBIB (2.9 µL of 100× stock), Cu-EDTA (10 µL of a 200× aqueous stock) or Cu-TMPA (10 µL of a 200×DMF stock), and a balance of SBM lacking trace mineral mix. Final concentrations were lactate (20 mM), fumarate (40 mM), OEOMA$_{500}$ (0.1 M), HEBiB (0.1 mM), and Cu-EDTA (0.2 µM) or Cu-TPMA (2.0 µM). For reactions with different carbon sources, lactate was replaced with sodium pyruvate (20 mM) or sodium acetate (20 mM). Polymerization was initiated by adding 20 µL of 200× cell stock (OD600=2.0) to bring the final reaction volume to 2 mL and starting bacterial OD600 to 0.02. Final reaction mixtures were incubated at 30° C. (*S. oneidensis*) or 37° C. (*E. coli*). Time points were aliquoted, diluted with deuterium oxide or GPC solvents, exposed to air to quench the reaction, then flash frozen in liquid $N_2$. Aliquots were stored at −20° C. until analysis via NMR spectroscopy or GPC.

Example 3

Polymerization of Diblock Copolymer

The polymerization of OEOMA$_{500}$ was initiated as the conditions illustrated above. After the complete depletion of OEOMA$_{500}$ (confirmed by NMR), a 2 mL mixture of NIPAM (22.6 mg, 0.1 M), 60% w/w sodium lactate solution (5.7 µL, 20 mM), 1 M fumarate solution (80 µL, 40 mM), Cu-TMPA (10 µL of a 200×DMF stock, 2 µM), and a balance of SBM lacking trace mineral mix were added to above reaction medium. The reaction was kept at 30° C. overnight. Aliquots were removed at fixed time points, diluted with deuterium oxide or GPC mobile phases, exposed to air to quench the reaction, then flash frozen in liquid $N_2$. Aliquots were stored at −20° C. until analysis via NMR spectroscopy.

Example 4

SEM Analysis of Bacteria Before/After Polymerization

Bacterial cells before/after polymerization were fixed in a 2% formaldehyde (0.85% NaCl) solution for 2 hours. The cell suspension was rinsed with fresh buffer (0.85% NaCl) and pelleted by centrifugation (6000×g, 20 min, 3×). Aqueous buffer solution was slowly exchanged with ethanol using a series of ethanol dilutions (20%, 40%, 60%, 80% and 100%) with pelleting in between (6000×g, 20 min). The ethanol solution of concentrated cell suspension was drop-cast onto glass, dried under ambient conditions, and sputter-coated with Pt before SEM analysis.

Example 5

Polymerization Controls

MR-1 and *E. coli* polymerization controls (cell supernatant, heat-killed, and lysed cells) were performed using the standard reaction conditions described above. All cellular samples were grown anaerobically to stationary-phase. Cell supernatant was obtained after centrifugation for 20 min at 6000×g. The supernatant was aspirated and passed through a 0.22 micron filter to sterilize after which 200 μL of saturated growth supernatant was added to each 2 mL polymerization reaction. Heat-killed cells were incubated in a block heater at 80° C. for 20 min, and cells were adjusted to a final OD of 0.02 in the reaction media. Lysed cells were obtained using a Branson Model 250 sonicator with a Model 102C Converter. Cells suspensions on ice were sonicated for 3 cycles of 5 s each. The solutions changed from opaque to clear, indicating cell lysis. The volume of cell lysate corresponding to a final OD of 0.02 of live cells in the reaction media was added to the polymerization mixture.

Example 6

Copper Treatment of $CF_4$ Loaded Bacterial

S. oneidensis was suspended in 1 mL SBM (OD600=0.2). 5 μL of 200× Cu(II) stock solution (0.4 mM, $CuSO_4.5H_2O$, Final Concentration=2 μM) was added to the above suspension and cells were incubated in the dark in an anaerobic chamber for 2 hours. The bacteria were pelleted (6000×g, 20 min) and resuspended in SBM. After repeating five times, the cells were concentrated via resuspension in 200 μL SBM. 1 μL of the dye CF4 or CF4_CTRL (1 mM stock) was mixed with 4 μL SBM to make the pre-mixed dye solutions. 2 pre-mixed dye solutions was added to the concentrated cell suspension (final dye concentration: 2 μM) and incubated in the dark for 15 min or 30 min. The bacteria were pelleted (6000×g, 20 min) and resuspended in 0.85% NaCl buffer to a cell density of ~$10^6$ cells/mL for analysis by flow cytometry. Cells were analyzed on a BD LSRFortessa SORP Flow Cytometer using an excitation of 561 nm and emission of 610/20 nm.

Example 7

Copper Detection by CF4 in Bacterial Supernatant

MR-1 was anaerobically cultured in 1 mL SBM (OD600=0.2). 2 μL CF4 or CF4-CTRL and/or 5 μL of 200× Cu(II) stock solution (0.4 mM, $CuSO_4.5H_2O$, Final Concentration=2 μM) were added to the cell suspension followed by incubating in the dark for 2 hours. Time points were obtained by pelleting a 200 μL cell suspension, aliquoting supernatant into a 96-well microplate, and measuring the fluorescence via plate reader ($E_{ex}$=536 nm, $E_{em}$=560-610 nm). Incubating with CF4 was necessary to prevent Cu(I) decomposition. TPMA was not included since it interfered with CF4-Cu(I) binding.

Example 8

Bacterial Growth/Viability Assessment

Competitive growth assays were performed in sterile 24-well plates, and OD600 was monitored by plate reader. Bacterial viability was determined by CFU counting and staining with the LIVE/DEAD BacLight Viability Kit (Invitrogen). For CFU counting, serial dilutions from the Cu-TPMA polymerization reaction and a control culture containing 20 mM sodium lactate and 40 mM sodium fumarate were plated onto LB agar containing 20 mM sodium lactate and 40 mM sodium fumarate, and incubated anaerobically for 18 hours. The LIVE/DEAD BacLight Viability Kit was used according to manufacturer instructions. Briefly, cells were harvested after polymerization and washed 3× with 0.85% saline by centrifugation at 6000×g for 20 min. Cells were concentrated to an OD600 of ~2.0 and incubated with the LIVE/DEAD BacLight Bacterial Viability dye mixture in the dark for 15 minutes. Excess, unbound dye was removed by repeated centrifugation and washing with 0.85% saline (total of 5 washes). 20 μL of cells were placed on glass slides, allowed to settle, and covered with a 0.17 mm coverslip. Excess moisture was wicked from the slide edges and the coverslips were sealed with nail polish. A Zeiss Axiovert 200M Fluorescent Microscope was used to image live and dead cells at room temperature. Images were captured using 475/40 nm excitation and 530/50 nm emission for green (live) fluorescence and 560/40 nm excitation and 630/75 nm emission for red (dead) fluorescence with a 40× oil objective. Cell counts to determine the viable population percentages were quantified by thresholding using Fiji 1.0 software from at least 3 different fields of view. Representative images were background subtracted using a rolling ball radius of 10 pixels in Fiji 1.0.

Example 9

Statistical Analysis

Unless otherwise noted, data is plotted and reported as the mean±S.D of N=3 replicates. Preliminary experiments indicated that this sample size would be sufficient to detect significant differences in mean values. Unless otherwise noted, P values were calculated using a two-tailed unpaired Students' t-test and OriginPro software.

Example 10

Extracellular Electron Transport Control Redox-Based Catalysis

To explore if extracellular electron transfer from MR-1 could control the performance of an exogenous metal catalyst, atom-transfer radical polymerization (ATRP) was employed as a model polymerization prototype. In ATRP, a redox-active metal catalyst reacts with a halogenated initiator to generate a radical that propagates through the addition of monomers or reacts with the newly oxidized catalyst to produce a dormant polymer chain (FIG. 1A). The concentration of active radicals and polymerization rate is controlled by the redox equilibrium of the metal catalyst, which can be influenced through the application of an external potential. This suggests that an electroactive bacterium with appropriate redox capabilities, such as MR-1, could control catalysis in a similar manner to an electrode via direct extracellular electron transfer to the metal catalyst. The results herein demonstrate that MR-1 can activate copper (Cu) catalysts for ATRP, and that this mechanism is coupled to bacterial metabolism via specific electron transport proteins. Organisms lacking analogous extracellular electron transport machinery, such as E. coli, showed minimal polymerization activity under the same conditions. Polymerizations in the presence of MR-1 exhibited rates comparable to other aqueous controlled radical polymerizations, and provided narrowly dispersed polymers with controlled molecular weights. The results demonstrate that extracellular electron transport can control redox-based catalysis.

Example 11

Background Free-Radical Polymerization is Insignificant

MR-1 was cultured under standard anaerobic conditions in the presence of poly(ethylene glycol) methyl ether methacrylate monomer with Mn=500 g/mol (OEOMA500) and a halogenated initiator (FIG. 1B). After 24 hours, the solution became viscous and almost complete conversion of monomer was measured using 1H NMR spectroscopy. As expected, no polymerization activity was observed under aerobic conditions. *Shewanella* basal medium (SBM) contains ethylenediaminetetraacetic acid (EDTA) and several redox-active metals, which could be functioning as catalysts. Culturing MR-1 in the absence of these metals did not affect growth rate on the time scale of our experiments, but significantly attenuated polymerization activity (FIG. 1C). Similarly, removal of initiator decreased monomer conversion after 24 hours of MR-1 culture, independently of metal presence. Cell-free and MR-1 supernatant controls showed minimal monomer conversion. Following the kinetics of the polymerization, the metals, initiator, and MR-1 were all found to give well-controlled first-order kinetics in OEOMA500 conversion, which is indicative of a constant radical concentration. Foregoing any of these components resulted in decreased monomer conversion and non-first-order polymerization kinetics. Together, these results reveal that a background free-radical polymerization does occur, but is insignificant under ATRP-relevant conditions. Furthermore, the free metal ion pool in MR-1 does not participate in catalysis, as evidenced by the significant decline in monomer conversion when exogenous metals were removed from the media.

Example 12

Cu(II/I) is an Active Catalyst for MR-1 Enabled ATRP

The identity of the metal source responsible for polymerization activity was then investigated. Polymerization activity was primarily attributed to *Shewanella*-induced reduction of Cu(II) to Cu(I). Indeed, almost complete rescue of polymerization activity was observed when all exogenous metals were removed from microbial culture except $CuSO_4 \cdot 5H_2O$ and EDTA (FIG. 1D). Although Cu(I) is a potent microbial toxin, minimal inhibition of MR-1 growth was observed after 24 hours of polymerization. The Cu(II/I) concentrations were also significantly lower than levels reported to induce a microbial stress response in MR-1. Notably, substituting *E. coli* (MG1655) for MR-1 under otherwise identical conditions completely abolished polymerization activity with Cu(II/I) as the catalyst (FIG. 1D). Additionally, no significant polymerization activity was observed under several alternative *E. coli* culture conditions. These data reveal that Cu(II/I) is an active catalyst for MR-1 enabled ATRP.

Example 13

MR-1 Extracellularly Reduces Cu(II)

ATRP activity in the model systems is contingent upon the MR-1 controlled reduction of Cu(II) to Cu(I). Thus, extracellular concentration of Cu(I) was measured using the Cu(I) specific fluorescent probe Copper Fluor-4 (CF4). Cultures of MR-1 were incubated with $CuSO_4 \cdot 5H_2O$ and CF4, spun down, and the extracellular concentration of Cu(I) measured via plate reader. Immediate reduction of Cu(II) was observed in the presence of MR-1, whereas *E. coli* controls showed minimal reduction on the same time scale (FIG. 1E). Using flow cytometry, no significant increase in cytoplasmic Cu(I) was measured following incubation of MR-1 with $CuSO_4 \cdot 5H_2O$ and CF4. This result demonstrates that there is effectively no free Cu(I) in bacterial cytoplasm under normal conditions, since it is immediately detected, sequestered, and trafficked to other cellular locations. These results confirm that MR-1 extracellularly reduces Cu(II), and explain the observed differences in polymerization activity between MR-1 and *E. coli*.

Example 14

Role of Ligand in Polymer Microstructure

Having demonstrated robust monomer conversion, the properties of polymers formed with MR-1, Cu(II), and EDTA were measured. Polymerization kinetics were well-controlled under these conditions but polymer molecular weights were higher than expected based on the monomer to initiator ratio. Similarly, a non-linear dependence of molecular weight on monomer conversion was identified. Under aqueous conditions, Cu(I) is prone to decomposition in the absence of a suitable ligand, which can lead to kinetic anomalies and uncontrolled molecular weights. Thus, the role of the ligand in polymer microstructure was examined. EDTA was replaced with tris(2-pyridylmethyl)amine (TPMA), a well-known ligand for aqueous ATRP, and an immediate increase in polymerization rate was observed. Complete conversion of $OEOMA_{500}$ occurred in ca. two hours while cell-free, supernatant, and *E. coli* experiments showed no significant conversion. A higher molecular weight macromonomer, $OEOMA_{900}$, showed similar polymerization kinetics in the presence of MR-1 and Cu(II/I)-TPMA. Under optimized conditions, precise control over poly($OEOMA_{500}$) molecular weight was achieved and a linear relationship between polymer molecular weight and conversion was measured (FIG. 2B). Repeated addition of $OEOMA_{500}$ to the microbial culture yielded first order-kinetics with rate constants consistent with the initial addition (FIG. 2C). Diblock copolymers were prepared via sequential addition of $OEOMA_{500}$ and N-isopropylacrylamide (NIPAM) to the MR-1 culture. Combined, these results demonstrate the living nature of the polymerization, highlight its synthetic utility, and definitively show that the reaction is metal-catalyzed.

Example 15

Secreted Reducing Factors are not a Significant Contributor to Polymerization

The biological factors that contribute to polymerization activity were examined. Specifically, cellular reductants and specific extracellular electron transport components (i.e. redox relevant proteins) were examined for possible roles in Cu(II) reduction and subsequent catalysis. The cytoplasm of bacteria is a reducing environment, easily capable of reducing Cu(II). Additionally, both *E. coli* and MR-1 can secrete reducing factors, such as glutathione, into the extracellular space. Secretion or release of metal ions, like Fe(II), could also be responsible for Cu(II) reduction. Under stress conditions, cell lysis and the secretion of reducing factors can influence the overall redox potential of a microbial culture. Indeed, polymerizations using glutathione as reductant showed dose-dependent polymerization activity, but polymerization was at least an order of magnitude slower relative to reactions containing MR-1. Lysed MR-1 and *E. coli* also showed significant polymerization activity, consistent with the release of intracellular reducing factors. However, heat-killed cells from both species, which are metabolically inactive but retain membrane structure, showed no detectable polymerization activity. Combined with the minimal activity of supernatant from active MR-1 cultures, these results demonstrate that secreted reducing factors are not a significant contributor to polymerization activity.

Example 16

Micro-Organism Viability Under Polymerization Conditions

To further assess the influence of cell lysis and Cu(II/I) toxicity on polymerization activity, MR-1 and *E. coli* viability under optimized polymerization conditions were evaluated. No significant difference in MR-1 colony forming units (CFUs) following polymerization was identified. Bacterial viability measurements, assessed via fluorescence microscopy, showed minimal loss in cell viability for both MR-1 and *E. coli* under typical polymerization conditions and corroborated our CFU counts. Scanning electron micrographs revealed that polymer was extracellular and closely associated with intact MR-1. Together, these data reveal that the Cu(II/I) concentrations (2 µM and below) and monomer/initiator used for the polymerizations did not elicit a stress response that can explain polymerization activity.

Example 17

Effect of Carbon Source and Loss of Key Proteins on Polymerization Activity

In order to investigate the role of extracellular electron transport and the extent of metabolic control over catalyst performance, the effect of carbon source and loss of key electron transfer proteins on polymerization activity were examined. Carbon source affects electron flux through the central metabolism of MR-1 and should influence polymerization rate if they are coupled (FIG. 3A). MR-1 fed with lactate, which generates 4 electron equivalents per molecule, yielded the highest rate of polymerization. By contrast, starved cells showed lower polymerization activity, as did cells fed with acetate, which can not be used as a carbon source by MR-1 (FIG. 3B). MR-1 supplied with pyruvate, which yields 2 electron equivalents per molecule, showed polymerization activity between lactate- and acetate-fed cells. Replacing TPMA with EDTA yielded a larger difference between lactate-fed and starved cells, likely because the longer timescale of these polymerizations (24 hours) accentuated metabolic differences. These results demonstrate that polymerization rate is strongly coupled to metabolic activity and subsequent electron flux.

Example 18

Effect of Loss of Key Proteins on Polymerization Activity

MR-1 uses specialized respiratory pathways to transport electron equivalents from the cytoplasm and periplasm to the extracellular space (FIG. 4A). To understand how these pathway components influence ATRP activity, the effect of knocking out select cytochromes and other redox-relevant proteins on polymerization kinetics was examined. Molecular hydrogen and flavins are strong reductants generated by MR-1 that may participate in Cu(II) reduction. However, knockouts of periplasmic hydrogenases (ΔhydAΔhyaB) and an inner membrane flavin exporter (Δbfe) exhibited no difference in monomer conversion when compared to MR-1. By contrast, a mutant lacking outer membrane cytochromes (ΔmtrCΔomcA) showed significantly attenuated polymerization rates (FIG. 4B). Notably, normal polymerization activity was partially rescued after complementation with a plasmid encoding MtrC (FIG. 4C). This demonstrates that polymerization activity can be controlled by manipulating MtrC expression. These results highlight the unique role that outer membrane cytochromes play in extracellular electron transport and offer additional support for a specific and manipulable link between metabolic activity and catalyst performance.

Example 19

Background Reactions Insignificant Relative to the Metal-Catalyzed Polymerization Although canonical ATRP activity was observed in the presence of MR-1 and a metal catalyst, initial experiments also confirmed the presence of a slow, background radical polymerization when a metal catalyst was absent. Several factors could contribute to the observed background activity or influence the metal-catalyzed polymerization. First, flavins can act as radical initiators in the presence of light and amines, but the low activity of MR-1 supernatant suggests that their inherent polymerization activity is relatively low under the examined conditions. Flavins can also participate in metal ion trafficking, but they are unlikely to compete with synthetic ligands for Cu(II/I) binding. Most importantly, a mutant with attenuated flavin export machinery (Δbfe) showed comparable activity to MR-1. In sum, these results indicate that flavins alone are not a significant contributor to polymerization activity. A second contributor to background polymerization activity may be direct radical initiation by outer-membrane heme-containing proteins, such as MtrC. Other heme-containing proteins have previously been used as catalysts for ATRP. However, the significant decrease in monomer conversion when exogenous metals were removed from solution suggests that it is primarily extracellular metal ions that act as catalysts, not outer membrane proteins. This is also corroborated by the dramatic increase in reaction rate that was observed upon switching the Cu(II/I) ligand from EDTA to TPMA. Finally, low concentrations of secreted metal ions, glutathione, or other small molecules could contribute to background polymerization activity. Dose-dependent polymerization activity was measured using glutathione as a reductant, but these reactions were significantly slower than those containing MR-1.

Example 20

Stress Response is a Minimal Contributor To Polymerization Activity

Cu(II) in the presence of EDTA was found to rescue polymerization activity relative to no-metal controls. However, Cu(II/I) is also a potent microbial toxin, particularly under anaerobic conditions. Similar to Fe(III/II), Cu(II/I) can participate in Fenton chemistry and contribute to oxidative stress. In addition, copper can readily replace iron in enzyme cofactors, such as those in fumarate reductase. It is possible that Cu(II) supplementation may induce cell lysis, thereby contributing to polymerization activity. However, the post-polymerization viability of MR-1 and *E. coli* was 74% and 86% respectively, suggesting that viable, metabolically active cells are controlling catalysis. Compared to other bacteria, MR-1 is extraordinarily sensitive to oxidative stress, which may explain the small differences in viability. Relative to *E. coli*, the metal ion homeostasis machinery of MR-1 is not well-characterized. However, MR-1 does possess homologs of CopA and CusA, which transport Cu(I) out of the cytoplasm at the expense of ATP hydrolysis or proton motive force respectively. The expression of these proteins was upregulated when MR-1 was exposed to exogenous copper (25 µM), but currently-employed Cu(II/I) concentrations were significantly lower (2 µM). Additionally, Cu(II) concentrations as low as 0.2 µM were found to induce polymerization (FIG. 1D).

Example 21

Effect of Metal Supplementation on Metal Homeostasis

While cell viability is maintained under polymerization conditions, Cu(II) supplementation may change bacterial physiology. In eukaryotic systems, incubation with exogenous copper results in a measurable increase in free cytoplasmic Cu(I). By contrast, bacteria quickly detect and sequester free Cu(I). Copper is an essential microbial nutrient, but the effective concentration of free Cu(I) in the cytoplasm is estimated to be in the attomolar ($10^{-18}$ M) range and is difficult to detect. Under stress conditions, including antibiotic exposure, copper homeostasis is disrupted and changes in cytoplasmic Cu(I) can be detected. When MR-1 was incubated with exogenousCu(II), no significant increase in cytoplasmic Cu(I) was deteted. By contrast, a significant increase in extracellular Cu(I) was measured and is indicative of electron transfer from MR-1. A similar increase was not seen when Cu(II) was incubated with *E. coli*, which lacks the extracellular electron transport machinery of MR-1. Although no changes were observed in cytoplasmic Cu(I), disruption of metal ion homeostasis could explain the small kinetic differences between the knockout and complementation studies, since the latter were conducted in the presence of antibiotic (kanamycin).

Example 22

Polymerization Kinetics

Radical polymerizations in the presence of MR-1 and Cu(II/I)-TPMA were well-controlled. The rate of the reaction was first-order with a rate constant comparable to polymerizations conducted in the presence of an external electrode. This is a characteristic feature of ATRP, and indicates that the concentration of radicals in the reaction is constant. Similar to electrochemical ATRP, only very low concentrations of catalyst were required for polymerization activity (0.2 µM). By contrast, polymerizations conducted in the presence of a sacrificial reductant require higher metal concentrations. Polymerizations in the presence of MR-1 yielded polymers with well-defined molecular weights and tight molecular weight distributions. Moreover, repeated addition of monomer showed that polymer chain ends were still active following initial monomer consumption. Both results, along with first-order kinetics, are characteristic of a living polymerization. It is noted that background free radical polymerization, such as the reaction observed in the absence of external metal ions, would not exhibit these properties. The synthetic utility of these polymerization reactions were demonstrated by preparing diblock copolymers with controlled molecular weight using poly(ethylene glycol) methyl ether methacrylate (average molecular weight 500, OEOMA$_{500}$) and N-icopropylacrylamide (NIPAM) as monomers. The preparation of diblock copolymers using monomers/oligomers having a large difference in molecular weights demonstrates that the presently claimed process lends itself to monomers having a wide molecular weight distribution range.

Example 23

Influence of Carbon Source

The rate of polymerization was strongly tied to carbon source. With TPMA as the ligand, lactate yielded the fastest polymerization rate, while acetate and starved cells showed the slowest rates. The residual activity observed in starved and acetate-fed cells is likely due to latent metabolic activity from growth in rich media or from residual electron density on the outer membrane cytochromes, both of which have been observed for MR-1 and *Geobacter sulfuredducens*. The reactions conducted using TPMA were relatively fast, and concluded in <2 hours. By contrast, more significant differences between lactate-fed and starved cells were observed when EDTA and longer polymerization timescales were used. The EDTA experiments also suggest that continuous metabolic activity and associated Cu(II) reduction counters catalyst deactivation when a less supportive ligand is used. The metabolic pathways that control electron flux can influence metal reduction and associated polymerization activity. Because the carbon source influences polymerization kinetics, the carbon source can be selected to rationally select a desired polymerization rate. A variety of carbon sources can be examined for a set of polymerization conditions and correlated to a specific polymerization rate. Carbon sources such as hexoses (allose, altrose, glucose, mannose, galactonse, xylose, etc.), pentoses (arabinose, xylose, ribose, lyxose, etc.), and various metabolic pathway intermediates (lactate, pyruvate, citrate, oxaloacetate, etc.) may be correlated with absolute or relative polymerization rates. The carbon source may then be chosen to select a desired reaction rate.

Example 24

Role Of MtrC

The decaheme cytochrome MtrC was determined to be important for polymerization activity. MtrC is a key decaheme c-type cytochrome through which MR-1 interacts with metals and metal oxides. *E. coli* cytochromes are not homologous to MtrC and the organism largely lacks the cytochrome content of MR-1 (42 cytochrome genes in MR-1 vs. 5-7 in *E. coli*). This deficiency in extracellular electron transport machinery explains why *E. coli* showed minimal polymerization activity. Complete abolishment of activity was not observed for the ΔmtrCΔomcA mutant because it is unlikely that Cu(II) reduction is completely tied to an exclusive cytochrome reduction pathway. MR-1 expresses several other electron transfer proteins that could mediate Cu(II) reduction, and their transcription levels appear agnostic toward different soluble electron acceptors. MR-1 also possesses outer membrane cytochromes other than MtrC (e.g. MtrF), which can compensate for its absence. All outer membrane cytochromes were inhibited using KCN, but these conditions disrupted positive polymerization controls.

Complementation of the ΔmtrCΔomcA mutant with a plasmid encoding MtrC rescued polymerization activity. This result is consistent with previous reports showing that MtrC alone is sufficient to rescue the majority of electron transfer activity and that OmcA is not required for the Mtr pathway to function. Although *E. coli* does not natively possess cytochromes that are homologous to MtrC, the Mtr pathway can be heterologously expressed in it, which offers a potential means to adapt the present polymerization system into non-*S. oneidensis* organisms. Alternatively, other electroactive bacteria with outer membrane cytochromes, such as *G. sulfurreducens*, could be used to control polymerization activity.

In electrochemical ATRP, polymerization activity is controlled by the structure of the metal catalyst and an externally applied potential. *S. oneidensis* (MR-1) can effectively control polymerization activity in the absence of an electrode via extracellular electron transfer to a redox-active metal catalyst. Polymers formed in the presence of *S. oneidensis* and Cu(II/I) were narrowly dispersed with defined molecular weights indicative of a living polymerization. Furthermore, polymerization kinetics were strongly dependent on catalyst structure, metabolic activity, and specific electron transport proteins.

Example 25

Catalyst-Free Background Polymerization

Figure 6:
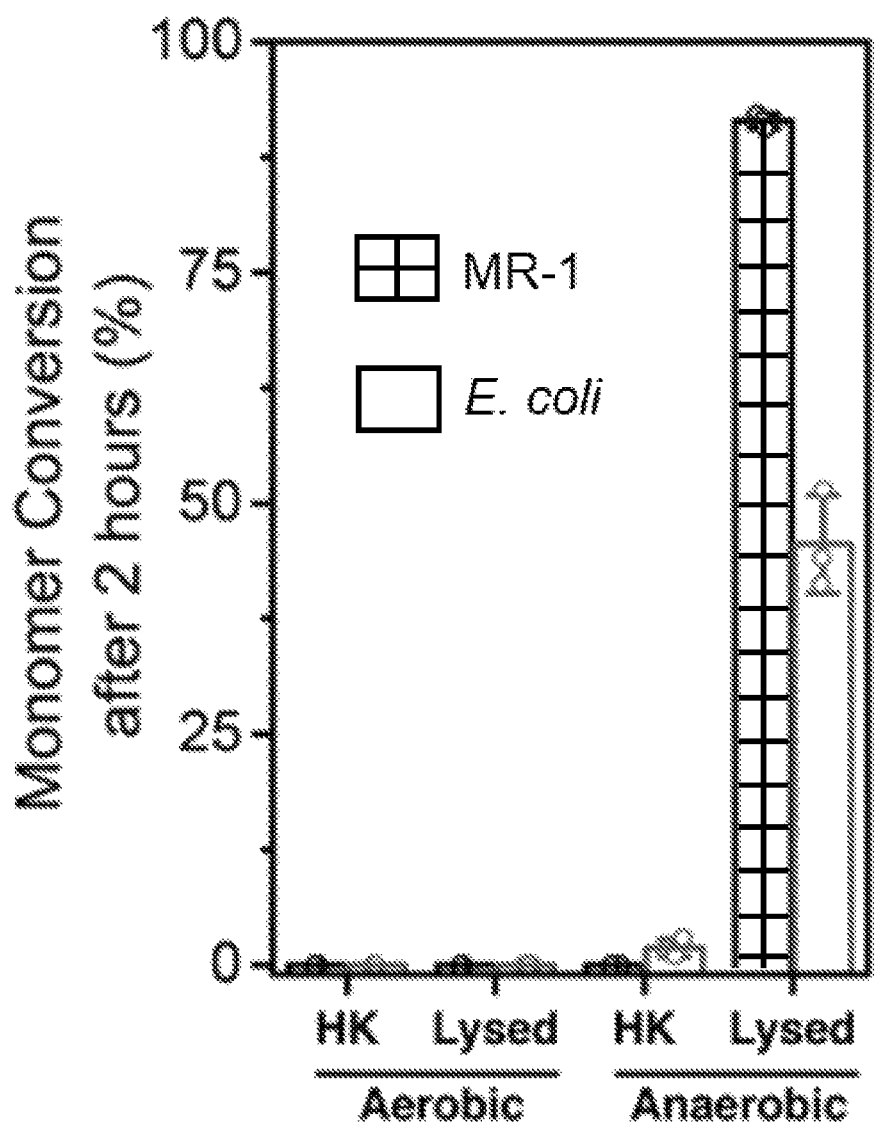
FIG. 6. Monomer (OEOMA$_{500}$) conversion using heat killed (HK) and lysed *E. coli* MG1655 or *S. oneidensis* MR-1 cells under anaerobic and aerobic conditions.

The roles of various polymerization components were analyzed. Previous experiments showed that a catalyst-free background polymerization proceeded to about 40% conversion under anaerobic conditions. In the experiments depicted in FIG. 5, catalyst-free polymerization reactions were run under aerobic conditions. Aerobic conditions completely suppressed this background polymerization, indicating that actively respiring cells, metal catalyst, and initiator are all required for significant monomer conversion. Similarly, aerobic conditions eliminated polymerizations caused by the release of cytosolic reductants following cell lysis (FIG. 6). These results confirm that in the absence of an active mechanism to remove dissolved oxygen, i.e., aerobic respiration, any initiation caused by adventitious radicals or uncontrolled reduction of the Cu catalyst is immediately quenched.

Figure 7:
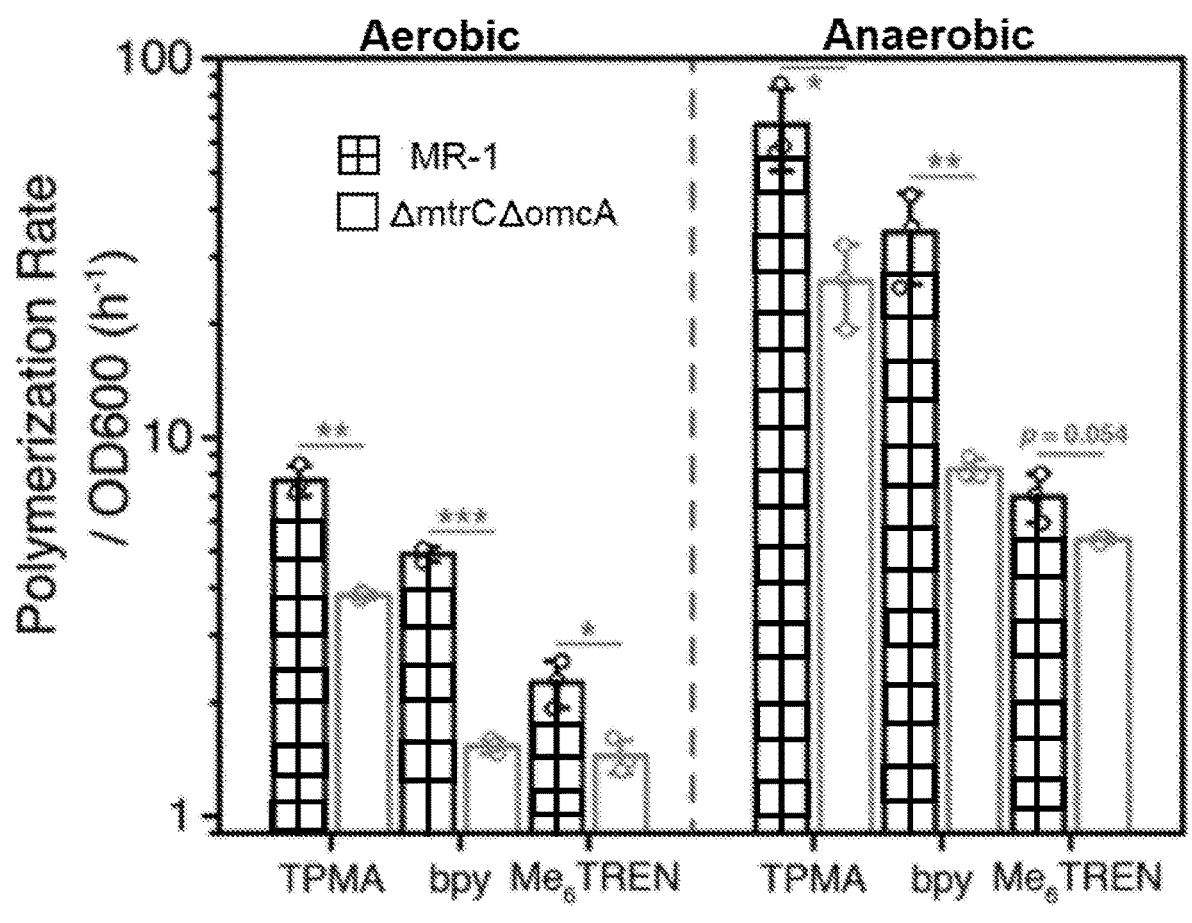
FIG. 7. Comparison of polymerization rate using MR-1 or ΔmtrCΔomcA and different Cu ligands normalized by initial cell inoculum (OD$_{600}$=0.02 for anaerobic, OD$_{600}$=0.2 for aerobic). Data show mean±SD of three independent experiments. *P<0.05, P<0.01, *P<0.001.

In general, polymerization rates under aerobic conditions were first order, indicating good control over radical concentration. As expected from the anaerobic experiments, polymerization rates under aerobic conditions were also dependent on inoculating cell density but generally required higher cell densities to efficiently remove oxygen. When normalized to initial cell density, aerobic polymerization rates were lower than those under anaerobic conditions, but still characteristic of a controlled polymerization (FIG. 7). Notably, polymerizations run in open containers were also successful, with measured rate constants consistent with reactions in closed vessels. Polymerizations were also tolerant to some increased oxygen mass transfer, as indicated by successful polymerizations in loosely-capped tubes at 100 RPM shaking. Overall polymerization rates using Cu(II)-TPMA and *S. oneidensis* MR-1 under aerobic conditions were largely comparable to rates using glucose oxidase and horseradish peroxidase (~1.5 h$^{-1}$ vs 0.56-5.9 h$^{-1}$ respectively) but at lower catalyst concentrations (~100 ppm vs 100-1000 ppm relative to monomer).

Under both aerobic and anaerobic conditions, polymerization rate could be varied over a wide range by changing the ligand for Cu. Surprisingly, rates decreased in the order TPMA>bpy>Me$_6$TREN. In an electrochemical cell under aqueous conditions, Me$_6$TREN previously displayed a faster polymerization rate compared to TPMA. These results indicate that in addition to affecting reduction potential, deactivation rate, and disproportionation propensity, the ligand environment around Cu may also influence its interaction with *S. oneidensis*' EET machinery. The specific role of MtrC (one of the terminal reductases that allows *S. oneidensis* to use metals and metal oxides as electron acceptors) was examined. *S. oneidensis* strains lacking mtrC (ΔmtrCΔomcA) showed significantly attenuated OEOMA$_{500}$ polymerization rates for all Cu catalysts tested. Using the lower molecular weight macromonomer OEOMA$_{300}$, ΔmtrCΔomcA and additional cytochrome knockout strains showed almost no appreciable activity under aerobic conditions. Together, these results highlight the extensive chemical (ligand structure) and biological (cell density and genotype) handles available for controlling polymerization activity under aerobic conditions.

Example 26

Polymerization Rates for Different Metal Salts and Metal Complexes

Figure 8A:
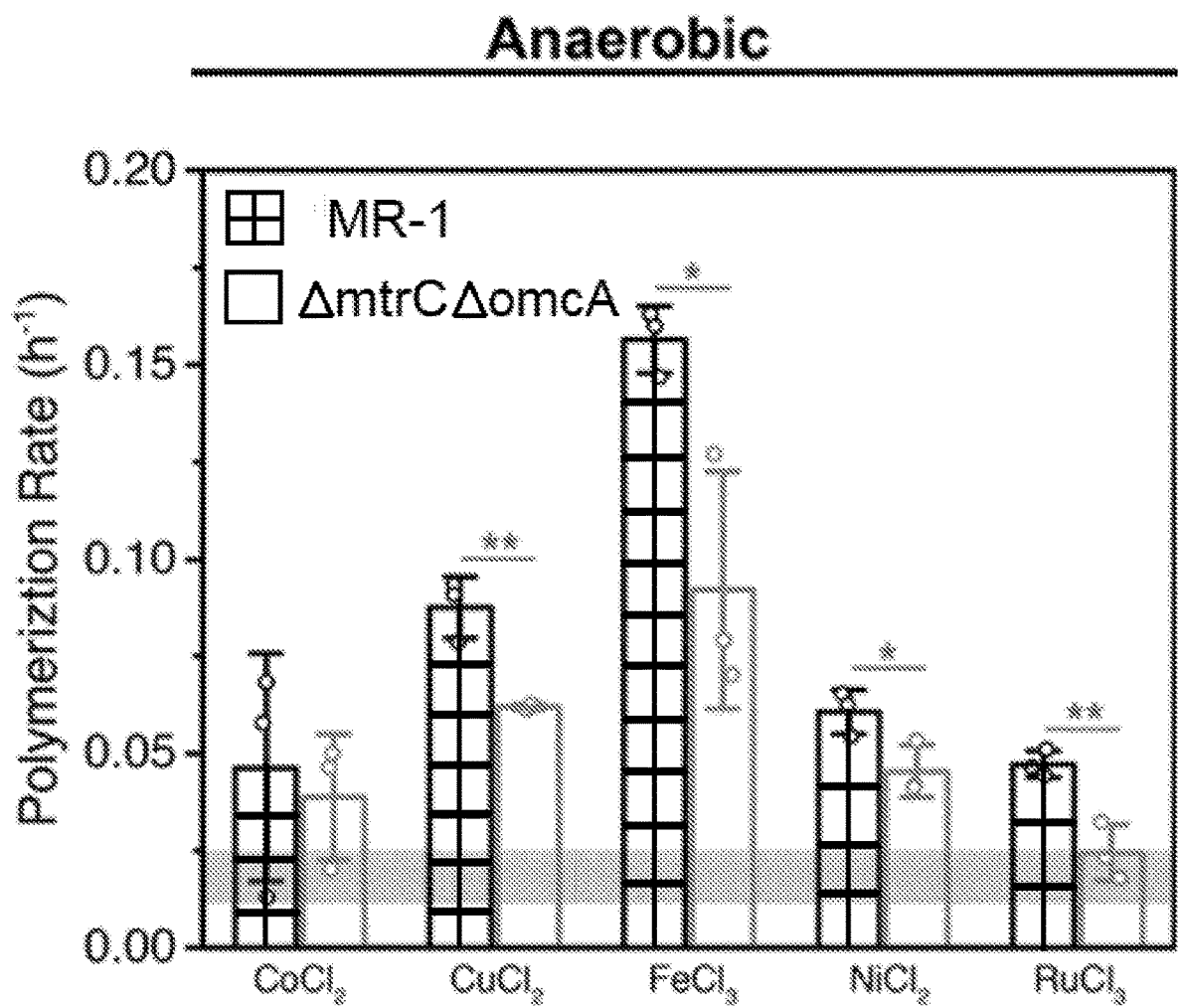
FIG. 8A-C. Different metal salts and catalysts. (A) Polymerization rates for different metal salts (2 μM) with EDTA and *S. oneidensis* strains (initial OD$_{600}$=0.02) under anaerobic conditions. The horizontal bar represents an estimated rate for the metal-free background polymerization. (B) Polymerization rates for different metal complexes (2 μM) and *S. oneidensis* strains (initial OD$_{600}$=0.02) under anaerobic conditions. (C) Polymerization rates for different metal catalysts (2 μM) and *S. oneidensis* strains (initial OD$_{600}$=0.2) under aerobic conditions. Data show mean±SD of three independent experiments. *P<0.05, P<0.01, *P<0.001.

Because polymerization is driven by EET flux to a metal catalyst, the effect of other metals besides Cu would on polymerization activity under both anaerobic and aerobic conditions was examined. Metal catalysts comprised of Fe, Co, Ni, and Ru have all been reported to exhibit ATRP-like activity, albeit with lower activity relative to Cu catalysts. Many of these metals can support *S. oneidensis* growth or lie within the redox range of its outer membrane cytochromes. As predicted, significant polymerization activity was achieved, relative to metal-free background controls, under anaerobic conditions for a variety of simple metal salts at low concentration (2 μM) using EDTA as ligand (FIG. 8A). Similar to the case with Cu catalysts, ΔmtrCΔomcA and *E. coli* MG1655 consistently showed reduced activity relative to MR-1 for most of the metals tested.

Figure 8B:
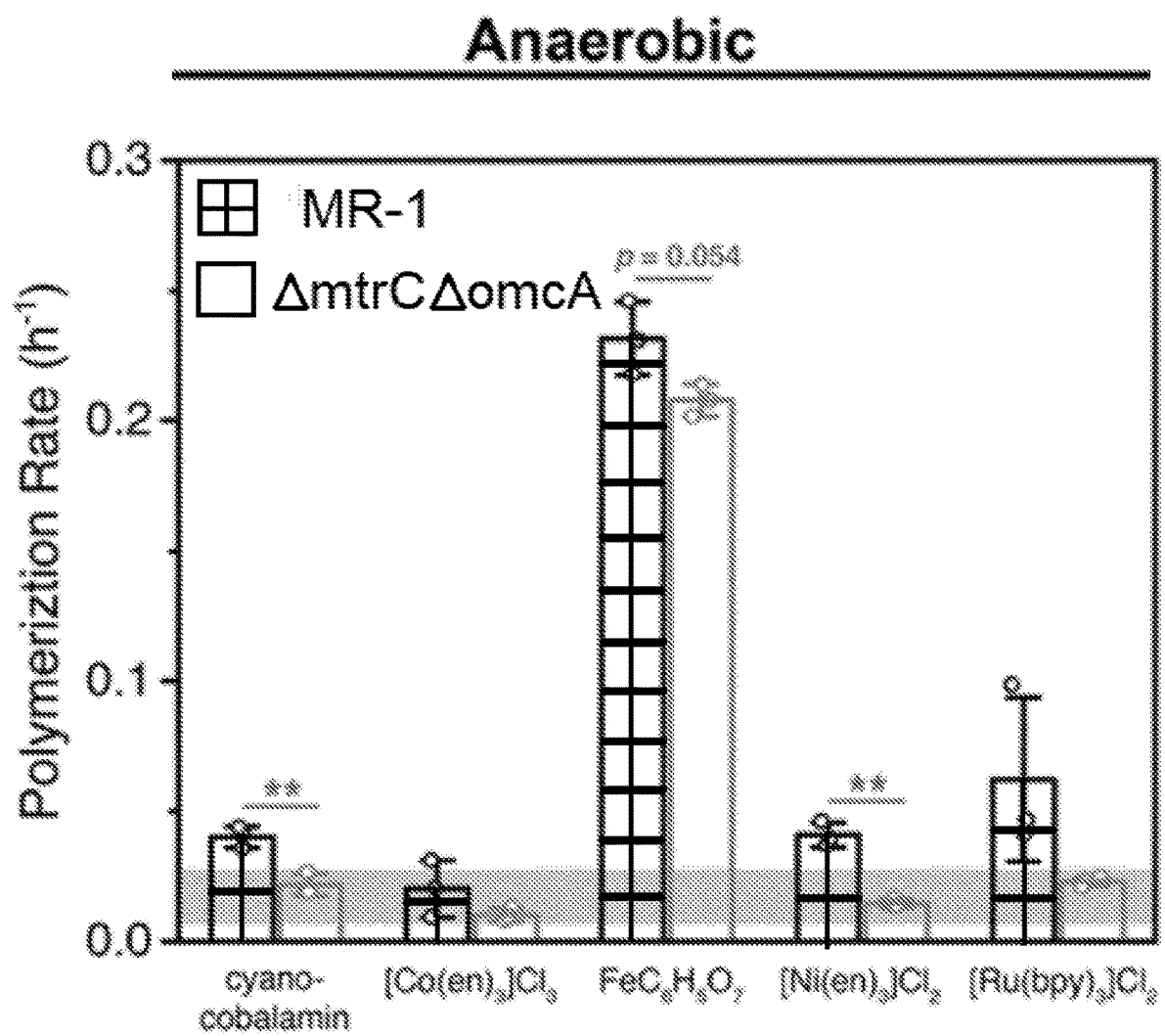
Figure 8C:
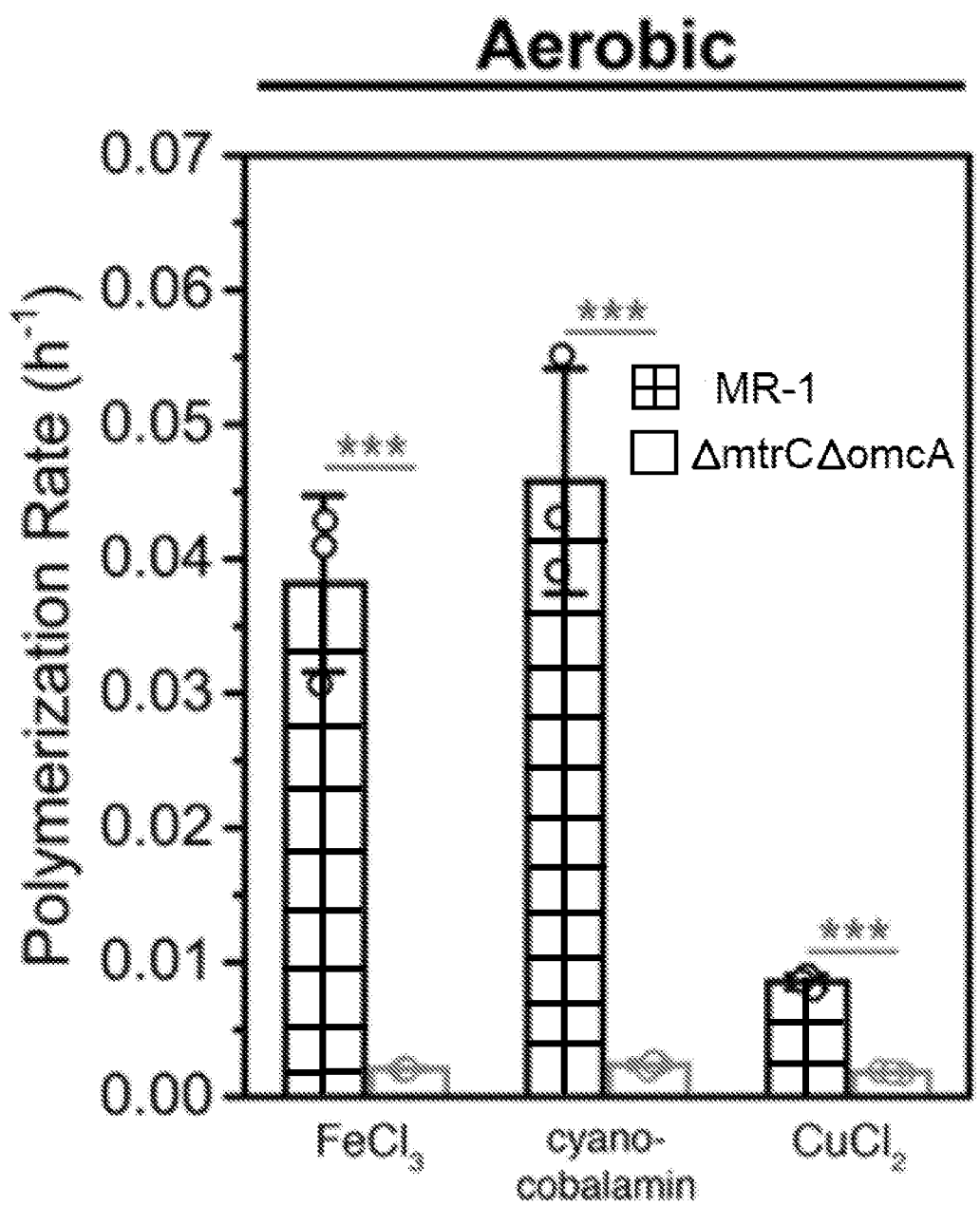

The effect of different, well-defined metal complexes was examined, including cyanocobalamin, [Co(en)$_3$]Cl$_2$ [en=ethylenediamine], FeC$_6$H$_5$O$_7$, [Ni(en)$_3$]Cl$_2$, and [Ru(bpy)$_3$]Cl$_2$ [bpy=2,2'-bipyridine]. With the exception of [Co(en)$_3$]Cl$_2$, all complexes showed activity above background levels in the presence of *S. oneidensis* under anaerobic conditions (FIG. 8B). Under more challenging aerobic conditions, only a handful of alternative metal catalysts at low concentration showed appreciable activity, with stark differences between MR-1 and the ΔmtrCΔomcA knockout (FIG. 8C). As predicted, aerobic polymerization rates for FeCl$_3$, cyanocobalamin, and CuCl$_2$ were lower compared to optimized Cu-based catalysts. Although fewer metals were active under aerobic conditions, additional ligand optimization or increasing catalyst concentration could improve activity, as was the case when EDTA was replaced with TPMA.

Example 27

Monomer Scope and Polymer Properties

Monomer scope and polymer properties were evaluated under both anaerobic and aerobic conditions. Cells were generally tolerant to many of the monomers tested, with little effect on viability. As a result, many of these monomers were amenable to microbial polymerization under anaerobic conditions. Even water insoluble and toxic monomers, like styrene, could be polymerized via emulsion polymerization, albeit with low yield. At low concentrations of Cu(II)-TPMA (2 μM), theoretical molecular weights were significantly higher than predicted, likely due to inefficient initiation. However, increasing the Cu concentration to 10 μM (~1.3 ppm) brought theoretical and predicted molecular weights into closer alignment while maintaining narrow polydispersities and having minimal effect on cell viability. These trends in molecular weight and polydispersity for the different monomers generally extended to aerobic conditions. Water soluble monomers including $OEOMA_{300/500}$, HEMA [HEMA=(hydroxyethyl)methacrylate], and NIPAM [NIPAM=N-isopropylacrylamide] yielded well-defined polymers near the targeted molecular weight under aerobic conditions. GPC traces for these polymers were also comparable to those from polymerizations conducted under anaerobic conditions. Narrow polydispersities for poly $(OEOMA_{300})$ were also obtained when $FeCl_3$ and cyanocobalamin were used as aerobic catalysts, although molecular weight was again higher than predicted. Using Cu(II)-TPMA, water insoluble monomers, including styrene and MMA, only yielded small amounts of polymer with non-ideal GPC traces under aerobic conditions. The performance of these monomers is attributed to a combination of poor solubility, the absence of surfactants in the media, cellular toxicity, and minimal liquid mixing. Nevertheless, the results indicate that *S. oneidensis* mediated polymerization is generally effective for a variety of monomers under both anaerobic and aerobic conditions.

Example 28

Oxygen Challenges

Enzymatic depletion of dissolved oxygen showed that polymerization can be automatically stopped and restarted in the presence of oxygen. Similarly, bubbling air through a monomer-containing microbial culture stopped polymerization, but polymerization proceeded at similar rates when bubbling stopped (FIG. 9A). This resumption of polymerization was also associated with increases in polymer molecular weight and indicates that the polymerization system can survive multiple oxygen challenges.

Example 29

Relationship Between Cellular Respiration and Polymerization Activity

The relationship between cellular respiration and polymerization activity was explored by employing different buffers, changing nutrient availability, and using lyophilized *S. oneidensis* cells. Using anaerobically pre-grown cells, the buffer made no significant difference in polymerization activity. Under anaerobic conditions, *S. oneidensis* is already expressing a proteome optimized for metal reduction, including the Mtr pathway. Consistent with the important role of functional metal reduction pathways, cells pre-grown in media lacking iron showed reduced polymerization activity, indicating they were unable to obtain enough iron to construct components of the Mtr pathway (e.g., hemes). By contrast to the anaerobic results, aerobic polymerizations were highly dependent on the choice of buffer. Polymerizations run in HEPES and PBS buffers showed reduced activity relative to *Shewanella* basal media (SBM) with casamino acids. A similar decrease in aerobic polymerization rates was observed when casamino acid was removed from SBM, which is consistent with previous reports showing that the absence of these nutrients significantly attenuates the specific growth rate of *S. oneidensis*. Because the aerobic polymerizations depend on the consumption of dissolved oxygen, media-related differences are believed to be tied to *S. oneidensis* metabolic activity and relative flux through the TCA cycle. Under ideal aerobic conditions growing on lactate, *S. oneidensis* diverts a significant fraction of metabolic flux (~50%) to the buildup of intermediates such as pyruvate and acetate. Similar to *E. coli*, the inclusion of casamino acids and other nutrients may allow *S. oneidensis* cells to devote more resources to bioenergy generation via respiration, in addition to increasing the specific growth rate. Under the present conditions, this translates to improved oxygen consumption and polymerization rates. Altogether, these results demonstrate how polymerization actively is closely coupled to aerobic and anaerobic respiratory pathways, both of which are engineerable components for tuning polymerization activity.

Example 30

Lyophilized Cells

A potential disadvantage of the polymerization system is that it requires pre-culturing of *S. oneidensis* or similar bacteria. To address this, lyophilized *S. oneidensis* cells were examined for their effect on aerobic polymerization (FIG. 9B). Using $OEOMA_{500}$ as monomer, lyophilized cells showed comparable aerobic polymerization activity to pre-cultured cells. In contrast to enzymatic methods for conducting aerobic radical polymerizations, viable cells could be collected from the polymerization mixture via centrifugation and reused for additional reactions after supplying fresh reagents. Reactions conducted in this manner showed comparable kinetics to reactions conducted with freshly cultured cells (FIG. 9C). Combined with the use of minimal media (SBM), this result demonstrates that the presently claimed polymerization system can be effective without prior microbiology experience and that simple bioreactor designs, such as fermenters, could potentially be adopted for polymerization reactions. Together, the use of minimal media, lyophilized cells, and the ability to survive repeated challenges with oxygen highlight the robustness and potential for scability of the polymerization system.

Example 31

Inducible Extracellular Electron Transfer Plasmids

Genetic (knockout/complementation of mtrC) and metabolic (use of various carbon sources) manipulations to *S. oneidensis* electron transfer can affect the rate of polymerization. To build upon this, new *S. oneidensis* strains exhibiting a spectrum of extracellular electron transfer properties were developed.

Figure 10:
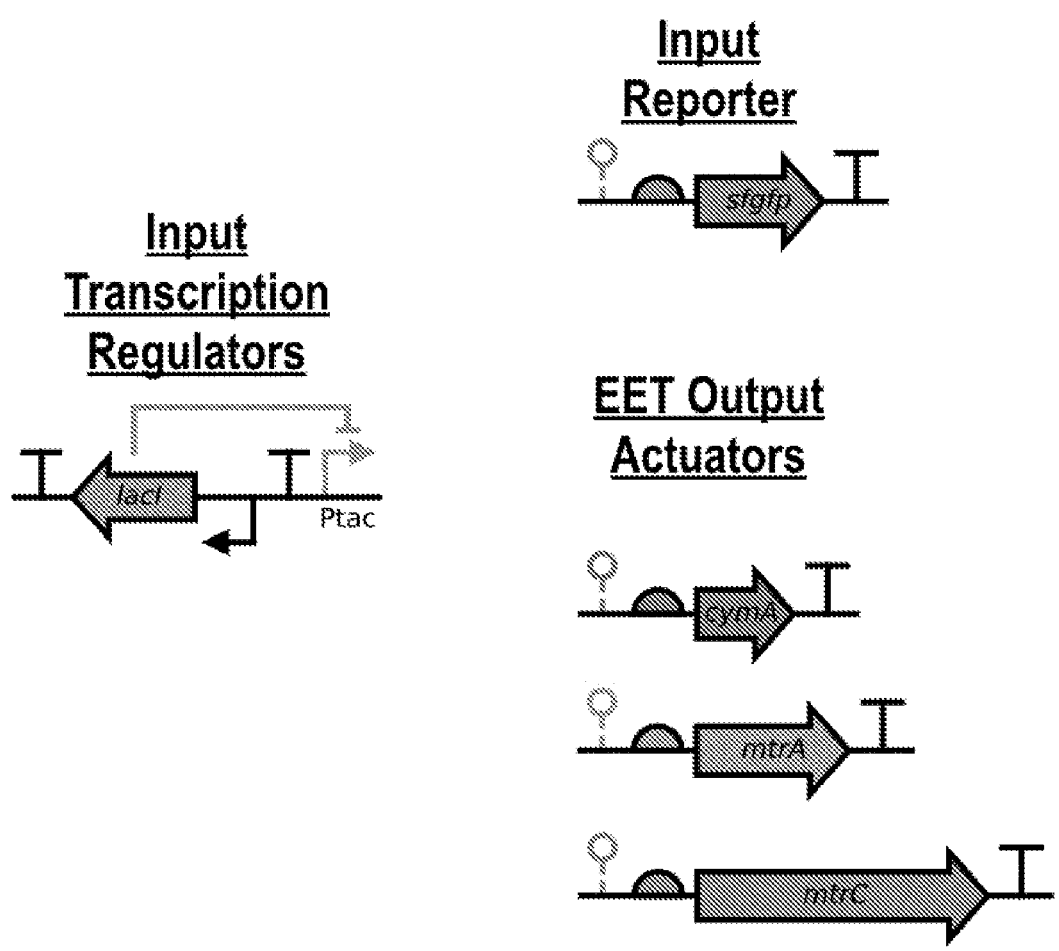
FIG. 10 Genetic circuit designs to control electron transfer activity. Genes are shown as thick arrows, promoters are shown as thin arrows, ribosome binding sites are shown as half-circles, ribozymes are shown as circles with broken tether, and terminators are shown as "T" symbols.

The new strains are *S. oneidensis* genomic knockouts (e.g., ΔmtrC, ΔmtrA, ΔcymA) transformed by newly designed plasmid DNA constructs encoding the knocked-out *S. oneidensis* extracellular electron transfer gene (e.g., mtrC, mtrA, cymA) under the control of variable strength gene expression elements, including inducible promoters and ribosome binding sites (FIG. 10). The new strains can be used to modulate polymerization activity.

The strains are *S. oneidensis* genomic knockouts (e.g., ΔmtrC, ΔmtrA, ΔcymA) transformed by newly designed plasmid DNA constructs encoding the knocked-out *S. oneidensis* extracellular electron transfer gene (e.g., mtrC, mtrA, cymA) under the control of variable strength gene expression elements, including inducible promoters and ribosome binding sites (FIG. 10). The plasmids contain modular DNA elements that insulate and tailor gene expression (e.g., unique terminators, self-cleaving ribozymes), thereby enabling the construction of more complex assemblies. Using these plasmids, simple logic gates can be generated which control gene expression, and thus electron transfer activity, based on the presence/absence of user-defined input signals.

Example 32

Buffer Gate Modulation of Gene Expression

Figure 11:
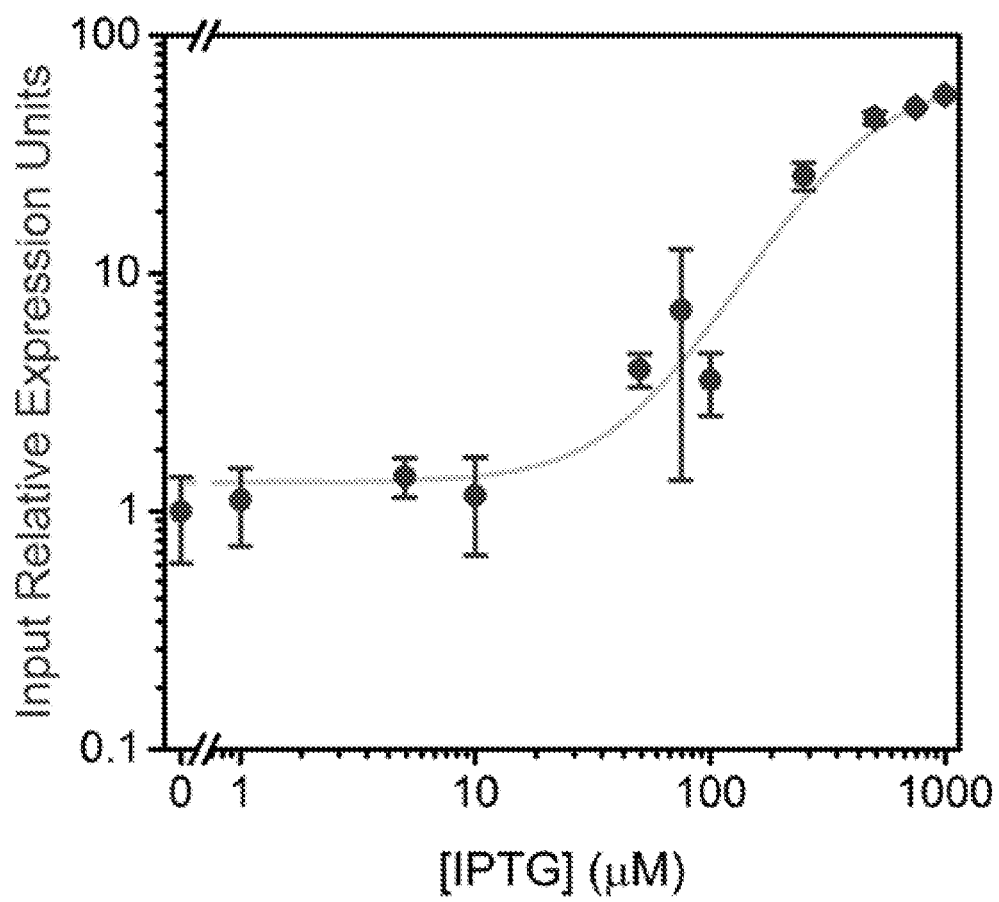
FIG. 11 BUFFER GATE/sfGFP Response Curve in *S. oneidensis* at various (Isopropyl β-D-1-thiogalactopyranoside) IPTG concentrations. Fluorescence was normalized to the uninduced strain and background was subtracted from a strain harboring an "empty" BUFFER GATE plasmid. Error bars indicate standard error the mean for three biological replicates.

An *S. oneidensis* strain/plasmid system was developed that tunes extracellular electron transfer via BUFFER GATE-controlled expression of mtrC. The BUFFER GATE sets gene expression as 'off' in the absence of a user-defined signal (e.g., small-molecule, light, heat). However, in the signal's presence, the BUFFER GATE turns gene expression 'on'. A BUFFER GATE was constructed by encoding the LacI repressor and Ptac promoter pairing on a plasmid, which together can modulate transcription of promoter-downstream genes based on culture concentration of the small-molecule Isopropyl β-D-1-thiogalactopyranoside or IPTG. To test the functionality and dynamic range of gene expression actuated by this BUFFER GATE, a plasmid was constructed that placed a ribozyme-insulated fluorescent reporter gene, superfolder GFP or sfGFP, downstream of the Ptac promoter. This BUFFER GATE/sfGFP plasmid was used to transform an *S. oneidensis* genomic knockout strain (ΔmtrCΔomcAΔmtrF) and sfGFP fluorescence was measured at various concentrations of IPTG. Using this *S. oneidensis* strain, 488/530 nm fluorescence varied over about 2 orders of magnitude (FIG. 11). This result successfully demonstrated that the LacI repressor/Ptac promoter BUFFER GATE could be utilized to modulate gene expression in *S. oneidensis*, as sfGFP fluorescence correlates to the RNA polymerase flux of the insulated gate at various IPTG concentrations, and the changes in gene expression should be comparable for similar ribozyme-insulated gene constructs.

Example 33

Control of MtrC Expression Modulates Dynamics of Fe(III)-Citrate Reduction

Using this BUFFER GATE plasmid design, sfGFP was replaced with mtrC and different strength ribosome binding sites (RBS) placed upstream of the mtrC gene were examined. The sequence of the RBS can predictably affect translation initiation rate (TIR) of the downstream gene and can be designed to rationally tune protein expression. Two mtrC BUFFER GATEs were constructed that differ only in RBS sequence, and, based on the computational predictions, vary over 5 orders of magnitude in TIR from one another. The 'strong' mtrC plasmid contains the B0032 RBS and has a predicted TIR of 13,644 a.u. The 'weak' mtrC plasmid contains a synthetic RBS sequence (sRBS1) that has a predicted TIR of 0.282 a.u. As a control, a BUFFER GATE plasmid that lacks any gene downstream of the Ptac promoter was constructed ('empty' plasmid). The ΔmtrCΔomcAΔmtrF strain was transformed with each of these plasmids to assay the dynamics of Fe(III)-citrate reduction in the presence/absence of IPTG. Wild-type *S. oneidensis* strain, MR-1, was also transformed with the 'empty' plasmid for comparison.

Using these four strains, anaerobic pregrowth in SBM medium containing 25 µg/mL kanamycin, 20 mM sodium lactate, and 40 mM sodium fumarate was set up in an anaerobic chamber. After 18 h, each strain was diluted 100-fold into wells of a 96-well plate. Each well contained SBM medium containing 25 µg/mL kanamycin. 20 mM sodium lactate, 5 mM Fe(III)-citrate, 1 mg/mL ferrozine, and ±1000 µM IPTG. The plate was set up in an anaerobic chamber and sealed using optically transparent covers and silicone oil around the edges, as to minimize exposure to oxygen. Once the anaerobic pregrowth was diluted, the sealed plate was immediately transferred to a fluorometric platereader maintained at 30° C. and the ferrozine/Fe(II) signal (562 nm) was continuously monitored. Fe(II) concentrations were determined using a standard curve set up in the same 96-well plate as the bacterial samples.

The MR-1 strain with the 'empty' plasmid and the ΔmtrCΔomcAΔmtrF strain with the 'empty' plasmid exhibited high and minimal Fe(III) reduction activity, respectively (FIG. 12). The ΔmtrCΔomcAΔmtrF strain carrying a mtrC plasmid with the 'strong' RBS sequence exhibited Fe(III) reduction activity in the absence of IPTG, likely due to leaky mtrC expression. In the presence of IPTG, this same strain showed a cessation of Fe(III) reduction after about 0.75 h. This was interpreted to result from the combination of high induction levels and strong translation initiation causing metabolic burden and shutdown of extracellular electron transfer, likely due to cell death. However, the ΔmtrCΔomcAΔmtrF strain carrying a mtrC plasmid with the 'weak' RBS sequence exhibited comparable activity to the ΔmtrCΔomcAΔmtrF strain with an 'empty' plasmid in the absence of IPTG. In the presence of IPTG, this 'weak' RBS strain demonstrated a short lag time followed by an increase in Fe(III) reduction activity, i.e., what is expected with BUFFER GATE logic. These results indicate that the choice of RBS sequence can significantly affect the dynamics of extracellular electron transfer coupled to expression of mtrC. Additionally, since the 'weak' RBS lag time was comparable to the timeframe in which the 'strong' RBS strain exhibited cessation of Fe(III) reduction, this further suggests that Fe(III) reduction for the 'weak' RBS strain is based upon the expression of mtrC and can be controlled at the transcriptional level.

Example 34

Inducer Molecule Concentration Alters the Rate and Lag-Time of Fe(III)-Citrate Reduction The ability to tune Fe(III) reduction kinetics by titrating various concentrations of IPTG was examined (FIG. 13). Each sample tested demonstrated an increase in Fe(III) reduction after a lag time. Individual kinetic runs were fit to a first-order model and the rate constant was determined. This rate constant was next normalized by the starting amount of *S. oneidensis* biomass (i.e., initial optical density or OD6000). Each rate constant was further normalized by the average of the rate constant determined in the absence of IPTG. To calculate the lag time at each IPTG concentration, the line tangent to the half-way Fe(II) concentration between the maximum and minimum values was determined. The lag time was obtained from the x-intercept of this tangent line. The normalized reduction rate constant (essentially the Fe(III) reduction rate constant per cell) increased sigmoidally with increasing concentration of IPTG and fit well to a Hill model. The Fe(III) reduction lag time monotonically decreased with increasing concentration of IPTG. Taken together, these results indicate that the BUFFER GATE was able to 'turn on' Fe(III) reduction based on mtrC expression and that the expression strength was dictated by the inducer molecule (i.e., IPTG) levels. These results demonstrate that transcriptional and translational control of extracellular electron transfer dynamics and can be extended to atom or group transfer polymerization, as well as other applications that utilize *S. oneidensis* electron transfer.

The invention claimed is:

1. A method for polymerizing acrylate or methacrylate monomer comprising:
   providing a system comprising:
      an electrically active *Shewanella oneidensis* MR-1 bacterium;
      a Cu (II)-TPMA catalyst;
      one or more acrylate or methacrylate monomers; and
      a radical initiator; and
   allowing the acrylate or methylacrylate monomers to polymerize in the system,
   wherein the rate of polymerization of the acrylate or methylacrylate monomers occurs by first-order polymerization kinetics.

2. The method of claim 1, wherein the radical initiator comprises one or more radically transferrable atoms or groups.

3. The method of claim 1, wherein the system further comprises a lactate bacterium carbon source.

4. The method of claim 1, wherein the electrically active *Shewanella oneidensis* MR-1 bacterium comprises at least one knocked out gene selected from the group consisting of omcA, mtrC, mtrA, mtrB, mtrF, and cymA.

5. The method of claim 4, wherein the electrically active *Shewanella oneidensis* MR-1 bacterium further comprises a plasmid DNA construct.

6. The method of claim 5, wherein the plasmid DNA construct includes a gene that corresponds to the at least one knocked out gene.

7. The method of claim 6, wherein expression of the gene of the plasmid DNA construct is under the control of at least one of inducible promoters, repressors, ribosome binding site, and a small molecule.

* * * * *